US006489163B1

(12) United States Patent
Roy et al.

(10) Patent No.: US 6,489,163 B1
(45) Date of Patent: Dec. 3, 2002

(54) RIBOZYME MEDIATED INACTIVATION OF THE ANDROGEN RECEPTOR

(75) Inventors: Arun K Roy, San Antonio, TX (US); Shuo Chen, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/853,164

(22) Filed: May 8, 1997

Related U.S. Application Data

(60) Provisional application No. 60/016,590, filed on May 8, 1996.

(51) Int. Cl.$^7$ .............................. C12Q 1/68; C07H 21/00
(52) U.S. Cl. ........................ 435/375; 435/6; 435/91.31; 435/320.1; 435/325; 536/23.1; 536/23.2; 536/24.5
(58) Field of Search ..................... 435/6, 363, 172.3, 435/91.31, 320.1, 371, 69.1, 91.1, 440, 366, 325; 536/23.1, 23.2, 24.32, 24.3, 24.31, 24.33, 24.5

(56) References Cited

U.S. PATENT DOCUMENTS

| | | | |
|---|---|---|---|
| 5,372,996 A | * | 12/1994 | Labrie |
| 5,416,017 A | * | 5/1995 | Burton et al. |
| 5,496,698 A | * | 3/1996 | Draper et al. |
| 5,525,468 A | * | 6/1996 | McSwiggen |
| 5,556,956 A | | 9/1996 | Roy et al. |
| 5,614,620 A | * | 3/1997 | Liao et al. |
| 5,641,508 A | * | 6/1997 | Li et al. |
| 5,648,478 A | * | 7/1997 | Henderson |
| 5,728,815 A | * | 3/1998 | Chung et al. |
| 5,834,440 A | | 11/1998 | Goldenberg et al. |

FOREIGN PATENT DOCUMENTS

WO   WO 94/18835   *   9/1994

OTHER PUBLICATIONS

Stull et al., Antigene, Ribozyme and Aptamer Nucleic Acid Drugs: Progress and Prospects, Pharmaceutical Research 12 (4), 465–483 (1995).*
Marshall, Gene Therapy's Growing Pains, Science 269, 1050–1055 (1995).*
Song et al., Regulation of Androgen Action by Receptor Gene Inhibition, Ann New York Acad.. Sci. 761, 97–108 (1995).*
Branch, A Good Antisense Molecule Is Hard to Find, TIBS 23 (Feb. 1998).*
White et al., The TATA–Binding Is a General Transcription Factor For RNA Polymerase III, J. Cell Science, Supplement 16, 1–7 (1992).*
Cotten et al., Ribozyme Mediated Destruction of RNA In Vivo, The EMBO J. 8(12), 3861–3866 (1989).*
Albelda et al., "Gene therapy for lung disease: hype or hope," *Annals of Internal Medicine*, 132(8):649–660, 2000.
Amarzguioui and Prydz, "Hammerhead ribozyme design and application," *CMLS, Cell. Mol. Life Sci.*, 54:1175–1202, 1998.
Asahara et al., "Stem cell therapy and gene transfer for regeneration," *Gene Therapy*, 7:451–457, 2000.
Buchschacher and Wong–Staal, "Development of lentiviral vectors for gene therapy for human diseases," *Blood*, 95(8):2499–2504, 2000.
Chang et al., , "Molecular cloning of human and rat complementary DNA encoding androgen receptors," *Science*, 240:324–6, 1988.
Chang et al., "Structural analysis of complementary DNA and amino acid sequences of human and rat androgen receptors," *Proc. Nat'l. Acad. Sci. U.S.A.*, 85(19):7211–5, 1988.
Chatterjee et al., "Targeted overexpression of androgen receptor with a liver–specific promoter in transgenic mice," *Proc. Nat'l. Acad. Sci.*, 93:728–733, 1966.
Chen et al., "Catalytic cleavage of the androgen receptor messenger RNA and functional inhibition of androgen receptor activity by a hammerhead ribozyme," *Molecular Endocrinology*, 12(10):1558–1566, 1988.
Chen, "Molecular strategies for selective inhibition of androgen receptor gene expression," *A Dissertation presented to the Faculty of The University of Texas Graduate School of Biomedical Sciencs at San Antonio in partial fulfillment of the requirements for the degree of Doctor of Philosophy in Cellular and Structural Biology, Mar., 1997; Also*, vol. 58/03–B of Dissertation Abstracts International, p. 1103, 1997.
Chen and Roy, "Specific inactivation of the androgen receptor messenger RNA by a hammerhead ribozyme," *Premier Event in 10$^{th}$ International Congress of Endocrinol.*, 10:87, Jun., 1996.
Eastham et al., "In vivo gene therapy with p53 or p21 adenovirus for prostate cancer," *Cancer Research*, 55:5151–5155, 1995.
Esquenet et al., "Control of LNCaP proliferation and differentiation: actions and interactions of androgens, 1α, 25–dihydroxycholecalciferol, all–trans retinoic acid, 9–cis retinoic acid, and phenylacetate," *The Prostate*, 28:182–194, 1996.
Fathman et al., "Gene therapy for autoimmune disease," *Clin. Immunol.*, 95(1):S39–S43, 2000.

(List continued on next page.)

Primary Examiner—John L. LeGuyader
Assistant Examiner—M Schmidt
(74) Attorney, Agent, or Firm—Williams, Morgan and Amerson

(57) ABSTRACT

The present invention provides synthetic ribozyme oligonucleotides alone and within constructs. The ribozyme gene provides methods for the treatment of prostate hyperplasia and other androgen dependent pathologies. Improved therapies for such diseases are provided without significant hormonal imbalance and without surgical intervention. Also provided are techniques for selecting and synthesizing effective and specifically targeted molecular tools for use in inhibiting androgen receptor gene expression.

21 Claims, 16 Drawing Sheets

OTHER PUBLICATIONS

Forster and Symons, "Self–cleavage of plus and minus RNAs of a virusoid and a structural model for the active sites," *Cell,* 49:211–220, 1987.

Franklin et al., "Prostate specific gene therapy using a novel PSA promoter: in vivo studies," *Proceedings of the American Urological Association,* 155:436A, 1996.

Hajjar et al., "Prospects for gene therapy for heart failure," *Circ. Res.,* 86:616–621, 2000.

Hanania et al., "Recent advances in the application of gene therapy to human disease," *Amer. Jrnl. Med.,* 99:537–552, 1995.

Haseloff and Gerlach, "Simple RNA enzymes with new and highly specific endoribonuclease activities," *Nature,* 334:585–591, 1988.

Hiltunen et al., "Insights into the molecular pathogenesis of atherosclerosis and therapeutic strategies using gene transfer," *Vasc. Med.,* 5(1):41–48, 2000.

Horoszewicz et al., "LNCaP model of human prostatic carcinoma," *Cancer Research,* 43:1809–1818, 1983.

Hrouda and Dalgleish, Gene therapy for prostate cancer, *Gene Therapy,* 3:845–852, 1996.

Huillier et al., "Efficient and specific ribozyme–mediated reduction of bovine α–lactalbumin expression in double transgenic mice," *Proc. Natl. Acad. Sci. USA,* 93:6698–6703, 1996.

Kaighn et al., "Establishment and characterization of a human prostatic carcinoma cell line (PC–3)," *Investigative Urology,* 17(1):16–23, 1979.

Kobayashi et al., "Reversal of drug sensitivity in multidrug–resistant tumor cells by an MDR1 (PGY1) ribozyme," *Cancer Research,* 54:1271–1275, 1994.

Marshall, "Gene therapy on trial," *Science,* 288:951–957, 2000.

Naldini et al., "In vivo gene delivery and stable transduction of nondividing cells by a lentiviral vector," *Science,* 272:273–267, 1996.

Nettelbeck et al., "Designer promoters for tumour targeting," *Trends in Genetics,* 16(4):174–181, 2000.

Pyle, "Ribozymes: a distinct class of metalloenzymes," *Science,* 261:709–714, 1993.

Russel and Cosset, "Modifiying the host range properties of retroviral vectors," *J. Gene Med.,* 1(5):300–311, 1999.

Sanda et al., "Demonstration of a rational strategy for human prostate cancer gene therapy," *Jrnl. Urology,* 151:622–628, 1994.

Sarver et al., "Ribozymes as potential anti–HIV–1 therapeutic agents," *Science,* 247:1222–1225, 1989.

Scanlon et al., "Ribozyme–mediated cleavage of c–fos mRNA reduces gene expression of DNA synthesis enzymes and metallothionein," *Proc. Natl. Acad. Sci. USA,* 88:10591–10595, 1991.

Sinnaeve et al., "Gene therapy in the cardiovascular system: an update," *Cardiovascular Research,* 44:498–506, 1999.

Snyder, "Adeno–associated virus–mediated gene delivery," *J. Gene Med.,* 1(3):166–175, 1999.

Steiner et al., "Gene therapy for the treatment of advanced prostate cancer by in vivo transduction with prostate–targeted retroviral vectors expressing antisense C–myc RNA," *Proceedings of the American Urological Association,* 155:340A, 1996.

Suzuki et al., "Adenovirus–mediated ribozyme targeting of HER–2/neu inhibits in vivo growth of breast cancer cells," *Gene Therapy,* 7:241–248, 2000.

Uhlenbeck, "A small catalytic oligoribonucleotide," *Nature,* 328:596–600, 1987.

Umekita et al., "Human prostate tumor growth in athymic mice: inhibition by androgens and stimulation by finasteride," *Proc. Nat'l Acad. Sci. USA,* 93(21):11802–11807, 1996.

Urtizberea, "Therapies in muscular dystrophy: current concepts and future prospects," *Eur. Neurol.,* 43:127–132, 2000.

Wu and Ataai, "Production of viral vectors for gene therapy application," *Biochemical Engineering,* 11:205–208, 2000.

Zabner et al., "Adenovirus–mediated gene transfer transiently corrects the chloride transport defect in nasal epithelia of patients with cystic fibrosis," *Cell,* 75:207–216, 1993.

\* cited by examiner

Substrate Specificity of Ribozymes

Ribozyme Driven by RNA Pol II Promoter Mediates
Reduction of AR mRNA in Transfected Cells

SEQUENCE LISTING

```
<160> NUMBER OF SEQ ID NOS: 15

<210> SEQ ID NO 1
<211> LENGTH: 19
<212> TYPE: RNA
<213> ORGANISM: HOMO SAPIENS

<400> SEQUENCE: 1
aucuugucgu cuucggaaa                                                       19

<210> SEQ ID NO 2
<211> LENGTH: 40
<212> TYPE: RNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 2
uuuccgaacu gaugaguccg ugaggacgaa acgacaagau                                40

<210> SEQ ID NO 3
<211> LENGTH: 7
<212> TYPE: DNA
<213> ORGANISM: ARTIFICIAL SEQUENCE
<220> FEATURE:
```

```
<221> NAME/KEY: misc_feature
<222> LOCATION: ()..()
<223> OTHER INFORMATION: SYNTHETIC OLIGONUCLEOTIDE

<400> SEQUENCE: 3 gctttgt                                                                      7

<210> SEQ ID NO 4
<211> LENGTH: 18
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 4
ttccgaactg atgagtcc                                                         18

<210> SEQ ID NO 5
<211> LENGTH: 18
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 5
agtgggagtg gcaccctt                                                         18

<210> SEQ ID NO 6
<211> LENGTH: 21
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 6
tgcgtgacat taaggagaag c                                                     21

<210> SEQ ID NO 7
<211> LENGTH: 20
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 7
atccacacgg agtacttggg                                                       20

<210> SEQ ID NO 8
<211> LENGTH: 40
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 8
tttccgaact gatgagtccg tgaggacgaa acgacaagat                                  40
```

```
<210> SEQ ID NO 9
<211> LENGTH: 40
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 9
atcttgtcgt tcgtcctca cggactcatc agttcggaaa                    40

<210> SEQ ID NO 10
<211> LENGTH: 19
<212> TYPE: RNA
<213> ORGANISM: Rattus rattus

<400> SEQUENCE: 10
aucgugucgu cuccggaaa                                          19

<210> SEQ ID NO 11
<211> LENGTH: 40
<212> TYPE: RNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 11
uuuccggacu gaugaguccg ugaggacgaa acgacacgau                   40

<210> SEQ ID NO 12
<211> LENGTH: 20
<212> TYPE: RNA
<213> ORGANISM: HOMO SAPIENS

<400> SEQUENCE: 12
ucuacccugu cucucuacaa                                         20

<210> SEQ ID NO 13
<211> LENGTH: 41
<212> TYPE: RNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 13
uuguagagac ugaugagucc gugaggacga aacaggguag a                 41

<210> SEQ ID NO 14
<211> LENGTH: 40
<212> TYPE: RNA
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 14
uuuccgaacu uaugaguccg ugaggacgaa ccgacaagau                   40

<210> SEQ ID NO 15
<211> LENGTH: 19
<212> TYPE: RNA
```

```
-continued
<213> ORGANISM: ARTIFICIAL SEQUENCE
<220> FEATURE:
<221> NAME/KEY: misc_feature
<222> LOCATION: ()..()
<223> OTHER INFORMATION: SYNTHETIC OLIGONUCLEOTIDE

<400> SEQUENCE: 15
uuuccgaaga cgacaagau                                                      19
```

RIBOZYME MEDIATED INACTIVATION OF THE ANDROGEN RECEPTOR

The present application claims priority to Provisional Application U.S. Serial No. 60/016,590, filed May 8, 1996. The government owns rights in the present invention pursuant to NIH grant number R37DK14744 and NIH grant number T32AG00165, National Institutes of Health).

FIELD OF THE INVENTION

The present invention relates to the field of selective inhibition of androgen receptor. The invention further relates generally to the field of gene therapy, and particularly gene therapy in the treatment of prostatic cancer.

BACKGROUND OF THE INVENTION

The prostate gland is an androgen-dependent organ and continues to grow with age. This leads to enlarged prostate in older men with consequent pathological manifestations. Androgen receptor is the principal mediator of prostatic growth.

A hammerhead ribozyme is a small RNA capable of cleaving a target RNA in a catalytic manner in the presence of a divalent cation (Pyle, 1993). Naturally occurring hammerhead ribozymes were discovered in certain plant viroids and viruses (Forster and Symons, 1987). The hammerhead ribozyme acts in "cis" during viral replication by the rolling circle mechanism. However a hammerhead ribozyme was engineered to cleave in "trans" against other RNAs (Uhlenbeck, 1987). A hammerhead ribozyme consists of antisense segments (stems I and III) and a catalytic domain (stem II). It can be designed to target specific mRNAs by selecting sequences flanking the catalytic element. The only requirement for the target substrate is the sequence HUX (H can be any nucleotide, X is A, C or U), where cleavage occurs after X (Haseloff and Gerlach, 1988). Hammerhead cleavage produces RNA products with 5' hydroxyl and 2', 3' cyclic phosphate termini (Buzayan, et al., 1986; Prody, et al., 1986). A hammerhead ribozyme has potential therapeutic applications, e.g., it inactivates specific RNAs in vivo, such as HIV-1 gene expression (Sarver, et al., 1990; Ojwang, et al, 1992; Yu, et al., 1993), RNAs responsible for other viral infections (Chen, et al., 1992; Sullenger and Cech, 1993; Tang, et al., 1994) and the RNA transcripts of other genes (Scanlon, et al., 1991; Kashani-Sahetet, et al., 1992; Lange, et al., 1993; Ha and Kim, 1994; Kobayashi, et al., 1994; Sioud, et al., 1994; Jarvis, et al., 1996; Ohta, et al., 1996; Sioud, 1996).

Androgen receptor (AR) is a ligand-activated transcription factor belonging to the steroid/thyroid hormone receptor superfamily (Evans, 1988; Beato, 1989). AR plays an important role in the coordination of the male-specific sexual phenotype and in the development of the male-reproductive organs such as the prostate gland (Quiley, et al., 1995). AR is expressed in various cells and tissues (Chang, et al., 1995; Roy and Chatterjee, 1995). It has also been considered as an etiologic factor for human benign prostatic hyperplasia (Brolin, et al., 1992; Wilding, 1992; Lepor, et al., 1993). Furthermore, AR gene mutations are involved in primary and secondary prostate cancer (Newmark, et al., 1992; Culig, et al., 1993; Suzuki, et al., 1993; Taplin, et al., 1995). A high expression of AR in recurrent prostate cancer cells and metastatic prostate cancer cells has also been observed (Taplin, et al., Viskarpi, et al., 1995; Umeki, et al., 1996). However, how the AR regulates differentiation and development of the male reproductive organs and its role in prostatic diseases are not known.

Clinical treatment of prostatic cancer has included the use of surgical techniques to remove enlarged prostate tissue, or the use of enzyme inhibitors such as PROSCAR™. PROSCAR inhibits 5-alpha reductase, which is the enzyme that converts testosterone to dihydrotestosterone. The abolition of testesterone itslf to induce androgen action limits the use and effectiveness of this therapy. These approaches are thus undesirable in many patients. Need continues to exist in the medical arts for a therapy that provides a more targeted approach to treatment of this pathology.

Androgen receptor plays a central role in the development, differentiation and maintenance of the male reproductive organs (Coffey, 1988; Griffin et al., 1989; Migeon et al., 1994). It is also involved in prostate disorders and other diseases (Edward, 1992; Macke et al., 1993; Qingley et al., 1995). The molecular mechanisms whereby AR regulates the physiological and pathological events are not clearly understood (Wilding, 1992; Lapor and Lawson, 1993). Hence, there has been no significant development of clinical approaches for treatment of prostate and related disorders.

SUMMARY OF THE INVENTION

The present invention describes inactivation of AR gene expression by engineering hammerhead ribozymes to cleave specific sites in AR mRNA. The present in vitro studies of hammerhead ribozymes reveal a high efficiency of such cleavage activity. The hammerhead ribozymes suppress AR mRNA expression in cultured cells.

Included in the present invention are hammerhead ribozymes that can selectively and efficiently degrade human androgen receptor messenger RNA. Also part of the present invention are expression vectors containing the gene for a ribozyme that, when introduced into a human prostate cancer cell, is capable of abolishing the androgen receptor mediated transactivation of a reporter gene. Targeting of the ribozyme gene into specific tissues of transgenic mice can be done to produce tissue-specific inactivation of androgen receptor. Therapeutic use of the ribozymes of the present invention to suppress androgen action in human clinical conditions such as the prostatic hyperplasia may be accomplished in vivo of the present invention.

The following provides three selection criteria in identifying and designing synthetic ribozyme of the present invention:

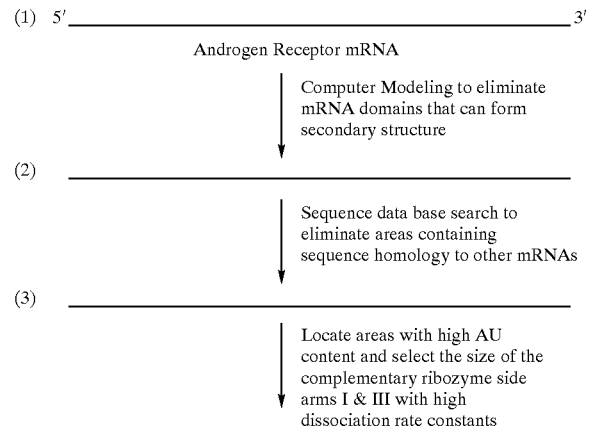

Based on these three selection criteria, the inventors designed three hammerhead ribozymes and tested their effectiveness in the in vitro endonuclease assay. One of these ribozymes, HR-2 was found to be particularly highly effective in selectively degrading the androgen receptor mRNA. This androgen receptor degrading ribozyme is more active than all ribozymes reported in the literature.

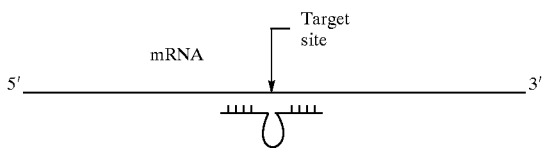

After eliminating sequence regions that can potentially form secondary structures or have significant homology to heterologous mRNAs, the inventors chose three structural domains of the AR mRNA with high AU contents as targets for the hammerhead ribozyme.

Hammerhead ribozymes are composed of two functionally distinct components; (i) the central catalytic core usually containing about 24 nucleotides with a conserved stem loop structure, and (ii) two variable specifier sequences on both 5' and 3' sides of the catalytic core that are complementary to the target RNA. The three targeted areas on the AR mRNA that were selected correspond to (i) transactivation domain of the rat AR (ribozyme, R-1), (ii) transactivation domain of the human AR (ribozyme, H-1), and (iii) the DNA binding domain of the human AR with 95% homology to the rat AR (ribozyme, HR-2). All three of these ribozymes contained 9–12 nt long specifier arms on each side of the catalytic core. Both ribozymes and truncated AR targets were cloned into the Bluescript vector and were transcribed with either T7 or T3 RNA polymerase for the in vitro endonuclease assay. At an equimolar enzyme-substrate ratio and at 37° C., R1 and H1 required ~4 hr for 75 to 100% cleavage of the substrate. The ribozyme HR-2 required less than 30 min for complete cleavage of the target substrate. The HR-2 ribozyme was also effective at a E:S ratio as low as 1:50. A mutant HR-2 containing two base substitutions within the catalytic core was enzymatically inactive and the wild type HR-2 did not act on substrates corresponding to R-1 and H-1, substantiating the specificity of the ribozyme function.

The inventors examined the effectiveness of the HR-2 in AR(-) PC3 (prostate cancer derived) cells transfected with the AR expression vector and a reporter construct containing MMTV-CAT. In this transfection assay an expression vector containing the HR-2 ribozyme was able to inhibit the AR mediated transactivation of the MMRV-promoter in a dose-dependent manner with a more than 95% inhibition at an AR:HR-2 ratio of 100. These results indicate that ribozymes can be an effective means for inactivating androgen action and are useful as a therapeutic agent when delivered to the target tissue through expression vectors and tissue-specific promoters.

By means of selection of the target base compositions (A-T, G-C pairs), the optimum size of the two sided arms, and the in vitro testing of various ribozyme constructs, the inventors have produced particular synthetic ribozymes having high activity and specificity for the human androgen receptor mRNA.

The inventors have developed the specifically active ribozyme HR-2 (SEQ ID NO:2) that cleaves the human androgen receptor mRNA (SEQ ID NO:1) at base positions 2374/2375 (Table 1). The nucleotide structure of the rat ribozyme (SEQ ID NO:1) and its complementarity to the rat androgen receptor mRNA target site (SEQ ID NO:10) are as follows:

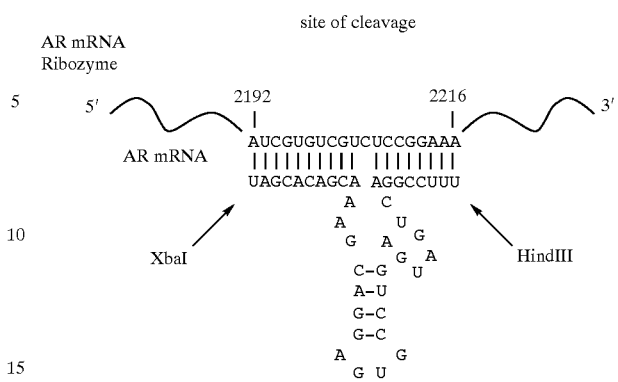

The in vitro cleavage of AR mRNA sequence by the ribozyme and kinetics of the endonuclease activity have established utility of the present invention.

Mammalian expression vectors containing the ribozyme HR-2 and a RNA polymerase II promoter derived from the cytomegalovirus (CMV) or a RNA polymerase III promoter derived from the gene for a small nuclear RNA (U6 RNA) when cotransfected into human (PC-3, prostate cancer derived) and rodent (3T3, mouse fibroblast derived) cells showed a dose-dependent inactivation of androgen receptor function.

This involved establishing:
 i) Cell transfection system.
 ii) Inhibition in the human prostate cancer cells by the CMV construct; and
 iii) Inhibition in the NIH 3T3 cells by the U-6 construct A transgenic mouse line containing selective overexpression of the androgen receptor in the liver targeted by the liver-specific phenylalanine hydroxylase gene promoter has been created by the present inventors. The same promoter is being used to target the HR-2 ribozyme to the liver. The homozygous AR transgenic mouse will be crossed with the HR-2 transgenic mice and the hepatic level of the androgen receptor in the hybrid mice will be monitored.

Gene therapy to suppress prostatic hyperplasia during old age and to destroy aberrant forms of androgen receptor mRNA in prostate cancer cells is thus available. This may involve therapeutic use of the ribozyme to suppress prostatic hyperplasia. Such can be performed by local delivery of the ribozyme gene construct inserted into any one of the emerging in vivo gene delivery vectors (for the most recent development see, Naldini et al., 1996) during cauterization of the enlarged prostate. At an advanced stage of prostate cancer the androgen receptor undergoes mutation and begins to function independent of the androgenic ligand (Taplin et al., 1995). Presently no specific therapeutic means to inhibit such an androgen-independent form of the receptor is available. The HR-2 ribozyme inserted into the appropriate delivery vector can be an effective drug to control such androgen independent mutant form of the receptor and to inhibit the resultant neoplastic prostate cell growth.

The present inventors demonstrate that two hammerhead ribozymes are able to cleave the RNA immediately following the GUC triplet sequences at positions 1393 and 2209 of the AR mRNA, respectively. Compared to a variety of other triplets, the GUC triplet preceding a particular site on the RNA substrate makes that site much more efficiently cleaved. (Haseloff and Gerlach, 1988; Ruffner et al., 1990; Shimayama et al., 1995; Hendrix et al., 1996). It can be demonstrated that the RNA phosphodiester bond immediately following the nucleotide residue, which has its ribose sugar group held in a south conformation (that is $C_2$.,-endo —$C_3$,-exo) is most preferably cleaved by the hammerhead ribozyme (Plavec et al., 1994). Furthermore, compared to other nucleotidyl 3'-ethylphosphates, cytidine 3'-ethylphosphate can most readily assume the south conformation at the ribose moiety, thus explaining the preference for C at the third base of the triplet preceding the cleavage site (Plavec at el., 1994). That G is the preferred first base in the marker triplet follows from the analysis of $K_{cat}$ and $K_m$ of the cleavage reactions using substrate in which the first base is changed from G to another base (Shimayama et al, 1995). The base preference at the first position of the triplet, despite its distance from the cleavage site, indicates that the entire triplet contributes to the structure of the transition state intermediate formed during the phosphodiester bond cleavage reaction (Hendrix et al, 1996).

Specificity and efficiency are also important parameters to consider in designing a hammerhead ribozyme. Factors, such as the secondary structure of the substrate and length as well as composition of the flanking sequences (stems I and III) of hammerhead ribozymes affect function. Many studies have shown that a hammerhead ribozyme targeted to a predicted open stemloop structure within target RNA substrate is more effective in catalyzing cleavage of the RNA substrate when it targets a base paired region (L'Huillier et al., 1992; Steinecke et al., 1994; Hendrix et al., 1996; Lieber and Strauss, 1996). Christoffersen and Marr found that this criterion applies well to ribozyme activity in cell culture and animal studies (Christoffersen and Marr, 1995). The length and composition of flanking sequences of a hammerhead ribozyme are also important factors in optimizing a designed hammerhead ribozyme. Although the length of the flanking sequences of the hammerhead ribozyme varies in different target sites, optimal cellular efficiency is observed with relatively short sequences of between 10–20 residues (Fedor et al., 1990; Herschlog, 1991; Heidenreich and Eckstein, 1992; Ferbeyre et al., 1996; Jarvis et al., 1996). Up to a point (~25 residues), longer flanking sequences can increase specificity of the hammerhead ribozyme, but it also decreases the cleavage efficiency, due to a decrease in turnover of the ribozyme (Heidenreich and Eckstein, 1992; Bertrand et al., 1994; Ferbeyre et al., 1996). This is supported by the further finding that reduced length of the flanking sequences between substrate and hammerhead ribozyme increases the rate of cleavage (Goodchild and Kohli, 1994). Composition of the flanking sequences is another consideration. A target region of RNA substrate with a high number of G or C residues so stabilizes interaction between the target and ribozyme that their separation after cleavage may be deterred (Bertrand et al., 1994). It is therefore preferable to select A/U rich flanking sequences since A:U base pair is weaker than G:C. Additionally, A-rich sequences in the flanks of the hammerhead ribozyme avoid the possibility of U-G wobble base pairing that can decrease discrimination between target sites (Hersalag, 1991; Bertrand et al., 1994). The MFOLD program was used to study the secondary structure of AR mRNA (Zuker and Stiegler, 1981; Zuker, 1989). Two cleavage sites of AR mRNA with open-loop or single-stranded regions were identified. The open regions contain GUC triplet sequences flanked by U-rich sequences that are not homologous to other gene sequences. Flanking sequences with 19 nucleotides and 18 nucleotides (stems I and III) were selected for HI and HR2 hammerhead ribozymes (FIG. 1) that contain 58% and 61% A/U-rich sequences, respectively. In the assay system, these hammerhead ribozymes were highly specific and catalyzed cleavage of only the AR mRNA substrate (FIG. 7).

Highly specific hammerhead ribozyme activity has been observed in cultured cells, and in animals (Saxena and Ackerman, 1990; Sullenger and Cech, 1993; Yu et al., 1993; Larsson et al., 1994; L'Hulillier et al., 1996). L'Hulillier et al. (1996) have observed that a hammerhead ribozyme cleaves only exogenous α-lac mRNA against which it was designed, and not against endogenous α-lac mRNA in transgenic mice, indicating the specificity of designed hammerhead ribozyme. In addition to these demonstrated specificities, the cleavage rate of both the HI and HR2 ribozymes is rapid and complete within 30 min at 1:1 molar ratio of ribozyme: substrate. However, compared to HI, HR2 is more efficient in vitro (FIG. 5) and in vivo (FIG. 8). The reason for the higher activity of HR2 over HI is not clear. One explanation could be that the target region in the AR mRNA for HR2 is more exposed than the target region for HI, so that HR2 has a better access to its RNA substrate (Kobayashi et al., 1994).

The following table enumerates several sequences that were used in the testing or development of the present invention.

TABLE 1

Identification of Sequences Having Sequence Identifiers

| SEQ ID NO: | SEQUENCE AND COMMENTS |
| --- | --- |
| SEQ ID NO:1 | 5'AUCUUGUCGUCUUCGGAAA-3' human AR mRNA target for HR-2 ribozyme |
| SEQ ID NO:2 | 3'UAGAACAGCA AAGCCUUU-5'<br>        A CUGA<br>        A    U<br>        G    G<br>        C    A<br>        A    G<br>        G    U<br>        G    C<br>        A    C<br>         GUG<br>HR-2 ribozyme |
| SEQ ID NO:3 | GCTTTGT U6 small nuclear RNA terminal site |
| SEQ ID NO:4 | 5'TTCCGAACTGATGAGTCC-3', primer from HR-2 hammerhead ribozyme stem I region |
| SEQ ID NO:5 | 5'-AGTGGGAGTGGCACCCTT-3'polylinker sequence in the pcDNA3 vector |
| SEQ ID NO:6 | 5'-TGCGTGACATTAAGGAGAAGC-3'primer of β-actin gene from position 667 to 687 |
| SEQ ID NO:7 | 5'-ATCCACACGGAGTACTTGGG-3'primer of β-actin gene from position 1063 to 1044 |
| SEQ ID NO:8 | 5'TTTCCGAACTGATGAGTCCGTGAGGACGAAACGACA AGAT 3', complementary DNA sequence for HR-2 ribozyme |
| SEQ ID NO:9 | 5'ATCTTGTCGTTTCGTCCTCACGGACTCATCAGTTC GGAAA 3', DNA coding sequence for HR-2 ribozyme |
| SEQ ID NO:10 | 5'AUCGUGUCGUCUCCGGAAA-3'rat AR mRNA target |
| SEQ ID NO:11 | 3'UAGCACAGCAAAGCAGGAGUGCCUGAGUAGUCAGG CCUUU-5', ribozyme for rat sequence |
| SEQ ID NO:12 | 5'UCUACCCUGUCUCUCUACAA-3'human AR mRNA target for H1 ribozyme |
| SEQ ID NO:13 | 3'AGAUGGGACAAAGCAGGAGUGCCUGAGUAGUCAG AGAUGUU-5', H1 ribozyme |
| SEQ ID NO:14 | 3'UAGAACAGCCAAGCAGGAGUGCCUGAGUAUUCAAG CCUUU-5', double mutant HR-2 ribozyme |
| SEQ ID NO:15 | 3'UAGAACAGCAGAAGCCUUU5', antisense oligo for HR2 |

BRIEF DESCRIPTION OF THE DRAWINGS

The following drawings are part of the present specification and are included to further demonstrate certain aspects of the invention. The invention may be better stood by reference to one or more of these drawings in combination with the detailed description of the specific embodiments presented herein.

In FIG. 2A, the wild-type and mutant hammerhead ribozymes with antisense specificity oligonucleotide elements were cloned into Hind III/Xba I sites of a mammalian expression vector (pcDNA3) under the control of the human CMV promoter driven by RNA polymerase II. In FIG. 2B, the wild-type and mutant hammerhead ribozymes with antisense oligonucleotides were cloned into Xba I/SAC I sites of the Bluescript vector containing the rat U6 small nuclear RNA promoter transcribed by RNA polymerase III. RZ, wild-type or mutant hammerhead ribozymes. AS, antisense oligonucleotide. BGH, bovine growth hormone. GCTTTGT (SEQ ID NO:3), U6 small nuclear RNA terminal site.

DETAILED DESCRIPTION OF THE PREFERRED EMBODIMENTS

Figure 11:
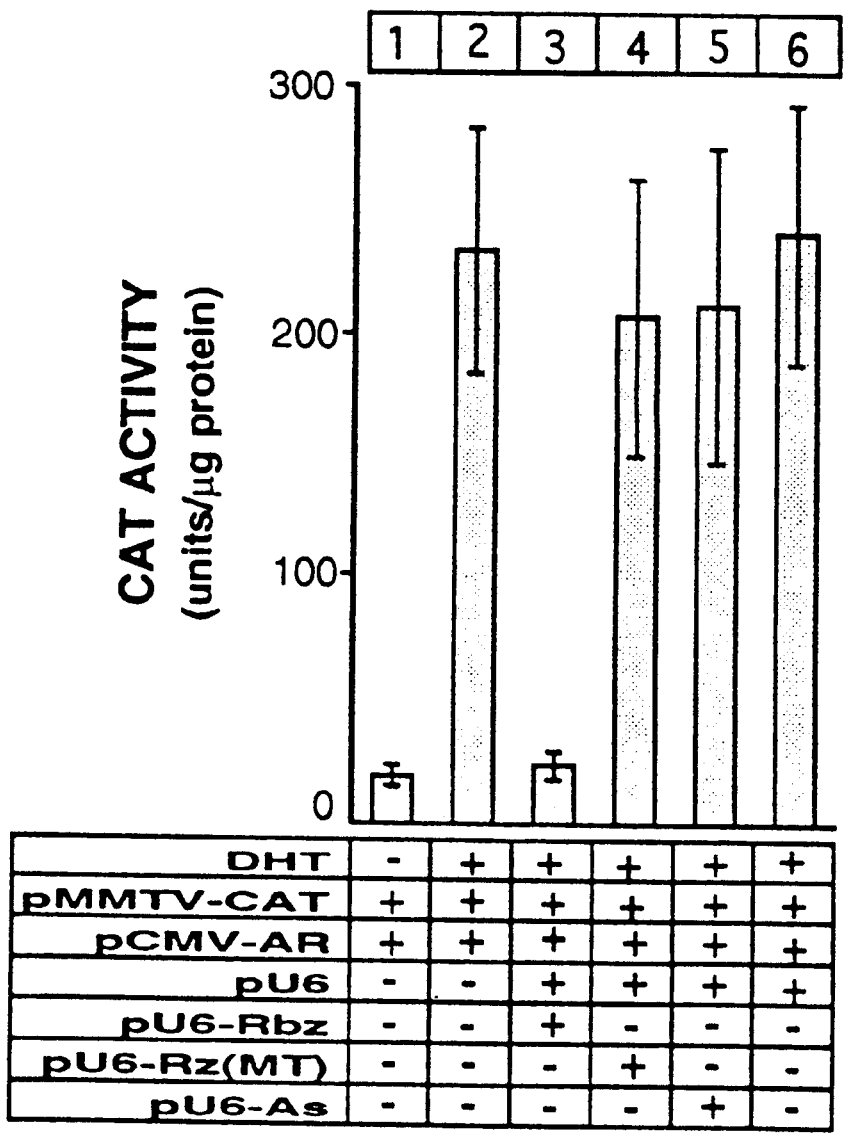
FIG. 11. Inhibition of androgen action by the HR2 hammerhead ribozyme under the control of the U6 small nuclear RNA promoter which is transcribed by RNA polymerase Ill. NIH 3T3 cells were transiently transfected with 2.51 μg of pCMV-AR as target and 3 μg of pMMTV-CAT as reporter along with either 13 μg of U6-HR2, or 13 μg of U6-mut-HR2, or 13 μg of U6-anti-HR2, or 13 μg of U6 control vector. DNA concentration was normalized to 20 μg with U6 control vector. After 48 hours, cells were harvested and CAT activity was measured by ELISA. The experiments were repeated at least three times. Experimental conditions are given at the bottom FIGS. 12A, 12B, 12C AND 12D. RNA polymerase II promoter-driven expression of the hammerhead and the ribozyme mediated reduction of AR mRNA transfected cells. The PC-3 cells were cotransfected with pCMV-AR and either pCMV-HR2, or pCMV-mut-HR2, or pCMV-anti-HR2, or pCMV control vector at 1:25, 1:50, 1:100 molar ratios. After 12 hours, total RNA was extracted, 12A and 12B. RNase protection assays were performed as described in materials and methods. $10^5$ cpm of the 179 nt fragment of anti AR mRNA probe and $10^5$ cpm of the 638 nt fragment of anti β-actin mRNA probe were hybridized With 8 and 1 μg of total RNA from different transfected cells. Protected RNA was analyzed on 5% polyacrylamide/8 M urea gels and exposed to X-ray film for 3 days (12A) and 1 day (12B). A. M. size marker. Lanes 1, 12; antisense AR RNA probe only. Lane 2; PC-3 cells transfected with pCMV-AR only. Lanes 3, 4 and 5; 1:25, 1:50, 1:100 molar ratios of pCMV-AR:pCMV-HR2. Lanes 6, 7 and 8; 1:25, 1:50, 1:100 molar ratios of pCMV-AR:pCMV-mut-HR2. Lanes 9, 10 and 11; 1:25, 1:50, 1:100 molar ratios of pCMV-AR:pCMV-anti-HR2. 12B is the same as 12A, but the probe was the anti β-actin mRNA 12C and 12D. Quantitative RT-PCR was performed. 200 ng of total RNA from transfected cells was subjected to RT-PCR. Primers from stem I sequences of the HR2 hammerhead ribozyme and sequences of pCDNA3 vector, and β-actin sequences were designed. One oligo of each pair of primers was labeled with [γ-$^{32}$P] ATP. The PCR products were separated on 5% polyacrylamide gels. The gels were dried and exposed to Xray film. 12C. Lane 1, RNA from PC-3 cells. Lane 2, RNA from PC-3 cells transfected with 0.5 μg of pCMV-AR vector. Lanes 3, 4 and 5; RNAs from PC-3 cells cotransfected with 0.5 μg of pCMV-AR and 12.5 μg, 25 μg and 50 μg of pCMV-HR2 vector, respectively. Lanes 6, 7 and 8; RNAs isolated from PC-3 cells that were cotransfected with 0.5 μg of pCMV-AR and 12.5 μg, 25 μg and 50 μg of pCMV-mut-HR2 vector, respectively. D is the same as C, but β-actin primers were used.

The examples presented herein are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.
Generation of the Constructs Four oligodeoxynucleotides (wild-type H1 (SEQ ID NO:13), wild-type HR2 (SEQ ID NO:2), mutant HR2 (SEQ ID NO: 14), and antisense oligonucleotide HR2 (SEQ ID NO:15); see FIG. 1; Table 1) were synthesized by phosphoramidite method and purified on a 16% polyacrylamide/ 8M urea gel. The oligonucleotides were tailed with recognition sequences for restriction enzymes, Sac I at their 5' ends and EcoR I at their 3'ends. Then, each oligonucleotide was ligated to a Bluescript SK plasmid (Stratagene, La Jolla, Calif.) that had been digested with SAC I and ECoR1, to allow expression of the hammerhead ribozymes or antisense oligonucleotides under the control of a T3 RNA polymerase promoter. A 144 bp segment of human AR cDNA containing a target site of the H1 hammerhead ribozyme, and a 234 bp segment of human AR cDNA containing another target site of the HR2 hammerhead ribozyme were also cloned into the Bluescript plasmid to generate AR mRNA in vitro. For in vivo study, the full-length human AR cDNA was cloned into a mammalian expression vector containing the human cytomegalovirus promoter to create pCMV-AR vector as a target. The mouse mammary tumor virus long terminal repeat promoter containing an AR response element was ligated with the chloramphenicol acetyl transferase gene (CAT) to create a pMMTV-CAT plasmid as a reporter. Hammerhead ribozyme elements, that is the wild-type H1 and wild-type HR2, the mutant HR2, and the antisense HR2 oligo—all have the flanking Hind III site at the 5' end and the Xba I site at the 3' end. Thus they could be cloned into the Hind II/Xba I sites of the pcDNA3 mammalian expression vector (Invitrogen, San Diego, Calif.), containing the CMV promoter, to create pCMV-H1, pCMV-HR2, pCMV-mut-HR2 and pCMB-anti-HR2 vectors. In order to generate pol II directing expression plasmid with the HR2 wild-type hammerhead ribozyme, mutant hammerhead ribozyme and antisense HR 2 oligo elements, the corresponding double-stranded DNA oligos were cloned in the Xba I/Sac I sites of a plasmid carries the rat U6 small nuclear RNA promoter upstream of the cloning sites (Das, et al., 1988). These constructs were designated as: U6-HR2, U6-mut-HR2 and U6-anti-HR2, respectively (FIG. 11). The sequences of all constructs were confirmed by DNA sequencing.

Assays of the Hammerhead Ribozyme Activity in Vitro

To generate transcripts in vitro, the Bluescript plasmids containing the AR cDNA and different hammerhead ribozymes were linearized with a restriction enzyme. The transcription reactions were carried out with T3 or T7 RNA polymerase as recommended by the supplier (Promega, Madison, Wis.). The AR gene transcripts were either labeled using $[\alpha\text{-}^{32}P]$ UTP, or synthesized with unlabelled NTPs. The products were purified by electrophoresis in a 10% polyacrylamide/8M urea gel. The AR mRNA substrate and the hammerhead ribozyme NA were incubated at 37° C. in 50 mM Tris-HCI, pH 7.5, 10 mM $MgCl_2$, 2 mM spermine and 1 mM EDTA. After adding stop buffer and heating at 95° C. for 2 min., the products were resolved y electrophoresis in a 10% polyacrylamide/8M urea gel. The products were detected by autoradiography or ethidium bromide staining. For time-course experiments, 100 µl of a mixture containing the hammerhead ribozyme and AR mRNA substrate was incubated at a 1:1 molar ratio at 37° under the conditions described above. The reaction was followed by removing 10 µl of the mixture at different times and the reaction was quenched by adding 5 µl of 10 mM EDTA/90% formamide/0.02% xylene cyano1/0.01% bromphenol blue. The labeled reaction products were separated on a 10% polyacrylamide/8M urea gel and quantified using a PhosphorImager (Molecular Dynamics, Inc., Sunnyvale, Calif.).

Kinetic Analysis

The mixtures of the HR2 hammerhead ribozyme (2 nM) and the AR mRNA substrates ranging from 8 nM to 70 nM were incubated at 37° C. in 50 mM Tris-HCI, pH 7.5, 10 mM $MgCl_2$, 2 mM spermine and 1 mM EDTA for 40 min. The reaction products were analyzed on a 10% polyacrylamide/8M urea gel and quantitated using a PhosphorImager (Molecular Dynamics, Inc.).

Cell Culture and Hammerhead Ribozyme Transfection Analysis

PC-3 cells which are AR negative and derived from human prostate adenocarcinoma were transfected using the calcium phosphate method (Chan, et al., 1995). Briefly, the PC-3 cells were plated, grown and cotransfected with a reporter construct (pMMTV-CAT), a target vector (PCMV-AR), and pCMV control vector together with hammerhead ribozyme expression vectors such as pCMV-H1, pCMV-HR2, pCMV-mut-HR2, pCMV-anti-HR2. After four hours, the transfection medium was replaced with normal growth medium with or without $10^{-9}$ M DHT. Cells were harvested 48 hours later and CAT activity analyzed. For stable transfection, rat AR cDNA was subcloned into a vector containing the neomycin gene (Invirogen, San Diego, Calif.). The vector containing the rat AR cDNA was transfected into a monkey kidney carcinoma cell line, CV-1. Transfected CV-1 cells were selected in 0.5 mg of G418/ml (Sigma, St. Louis, Mo.). Individual colonies were expanded and screened by RT-PCR. The pMMTV-CAT and pCMV control vectors were cotransfected with either pCMV-H1 or pCMV-HR2 into the stably transfected cells (CV-1/AR). NIH 3T3 cells were also used in cotransfection studies. After 12 hours, the medium was replaced with normal growth medium with or without $10^{-9}$ M DHT. The cells were harvested after 24 hours, and CAT activity was detected by the CAT-ELISA assay.

Total RNA Isolation

Total RNA from the transfected cells with or without hammerhead ribozymes was isolated according to the protocol provided in the Rneasy Kit (Qianga, Chatsworth, Calif.). Briefly, $10^6$ cells were washed three times with ice-cold PBS without $Ca^{++}$ and $Mg^{++}$, and then were lysed with an RLT buffer containing guanidinium isothiocyanate. The lysate was mixed with an equal volume of 70% ethanol and centrifuged through an Rneasy spin column. Impurities were removed from the column by washing it once with an RWI solution containing guanidinium isothiocyanate and twice with an RPE solution. Total RNA was eluted. The products were treated with Rnase-free pancreatic Dnassel (Promega) in 10 mM MgCl2/0.1 mM dithiothreitol/10 mM Rnase inhibitor for 30 min. at 37° C. (Ojwang, et al., 1992).

Rnase Protection Assays (RPAs)

To generate an antisense AR RNA probe, rat AR cDNA was digested with Sst I to release a 179 bp fragment between 1697 and 1865. The fragment was cloned into the SstI site of the Bluescript vector. The vector containing 179 bp fragment of the AR cDNA was linearized with Xba I and an antisense AR RNA probe was synthesized with $[\alpha\text{-}^{32}P]$ UTP, CTP, ATP and GTP and T7 RNA polymerase. The probe was purified through a 5% polyacrylamide/8M urea gel. The β-actin antisense RNA probe was also synthesized as an internal control. Rnase protection assays were performed using a ribonuclease protection assay kit RPAII (Ambion, Inc., Austin, Tex.). Briefly, 1 and 8 µg of total RNA were hybridized with $5\times10^5$ cpm of radiolabeled antisense β-actin RNA probe and 5×105 cpm of radiolabeled antisense AR RNA probe. The products were digested with a diluted RNaseA/T1 mixture and precipitated with ethanol. The protected AR mRNA and β-actin mRNA products were separated on 5% polyacrylamide/8 M urea gels. The gels were dried, and AR mRNA was quantitated using a PhosphorImager (Dynamic Molecule, Inc.).

Androgen receptor mRNA was normalized o β-actin mRNA in each sample.

Expression of the Hammerhead Ribozyme in Cultured Cells

In order to detect hammerhead ribozyme expression in transfected cells, 200 ng of total NA from different treated cells was subjected to RT-PCR using two primers, 5'-TTCCGAACTGATGAGTCC-3' (SEQ ID NO:4) from the HR2 hammerhead ribozyme stem I region (see FIG. 1) and 5'-AGTGGGAGTGGCACCCTT-3'(SEQ ID NO:5) from the polylinker sequence in the pcDNA3 vector. Two primers of β-actin gene, 5'-TGCGTGACATTAAGGAGAAGC-3' (SEQ ID NO:6) from position 667 to 687, and 5'-ATCCACACGGAGTACTTGGG-3' (SEQ ID NO:7) from position 1063 to 1044, were also synthesized for controls. One oligonucleotide of each primer pair was labeled with [$\gamma$-$^{32}$P] ATP and T4 kinase. The cycling conditions were as follows: 94° C. for 1 min, 57° C. for 1 min and 72° C. for 2 min for 21 cycles. The PCR products were separated in a 5% polyacrylamide gel, and specific bands were quantitated using a PhosphorImager. The expression of the hammerhead ribozyme in different treated cells was analyzed and normalized to $\beta$-actin RNA.

Immunohistochemical Analysis of AR

Immunohistochemical studies of PC-3 cells transfected with or without the hammerhead ribozyme were performed following the experimental conditions described (Doumit, et al., 1996). The cells were washed with PBS three times and fixed in PBS containing 2% paraformaldehyde and 10% sucrose, pH 7.2, for 20 min, then permeabilized in PBS containing 10% mouse serum for 30 min, and cells were incubated with primary AR antibody in blocking reagent overnight at room temperature. Then the cells were washed three times in PBS and exposed to biotinylated goat anti-rabbit IgG (1:100) as secondary antibody in vectastain elite ABC reagent (Vector Lab., Burlingame, Calif.) for 30 min at room temperature. After three washes in PBS, AR positive staining with the enzyme activity produced a brown reaction product when exposed to 3,3'-diaminobenzidine (Sigma, St. Louis, Mo.) containing $H_2O_2$.

Analysis of AR mRNA Secondary Structure

A Vax 8600 and a Vax 8800 computer with the sequence analysis software package from Genetic Computer Group (University of Wisconsin, Madison, Wis.) were used. Theminimal fee energy fold of AR mRNA was computed using MFOLD program version 8.1. the MFOLD program predicts optimal and suboptimal RNA secondary structures based on the energy minimum method (Zuker and Stieger, 1981; Zuker, 1989). Graphic representations were obtained using SQUIGGLES (University of Wisconsin, Madison, Wis.).

The following examples are presented only to describe preferred embodiments and utilities of the present invention, and are not meant to limit the scope of the present invention unless specifically indicated otherwise in the claims appended thereto.

EXAMPLE 1

The present example demonstrates the site specificity of the synthetic ribozyme of the invention.

Figure 15:
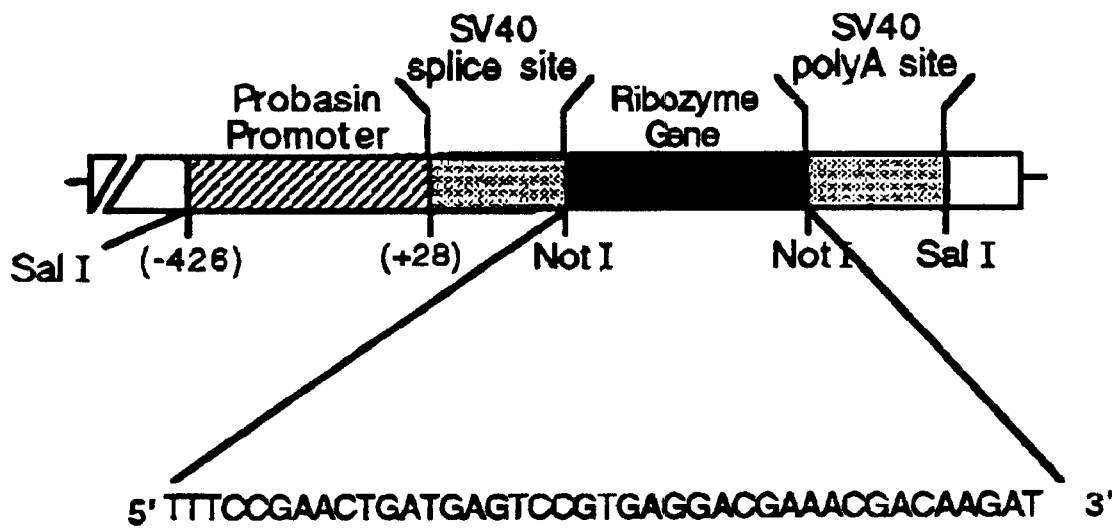
FIG. 15. Ribozyme gene construct with probasin promoter. The sequence shown is the 5' to 3' sequence for the HR-2 ribozyme (SEQ ID NO:8), the coding strand for which is SEQ ID NO:9.
Figure 16:
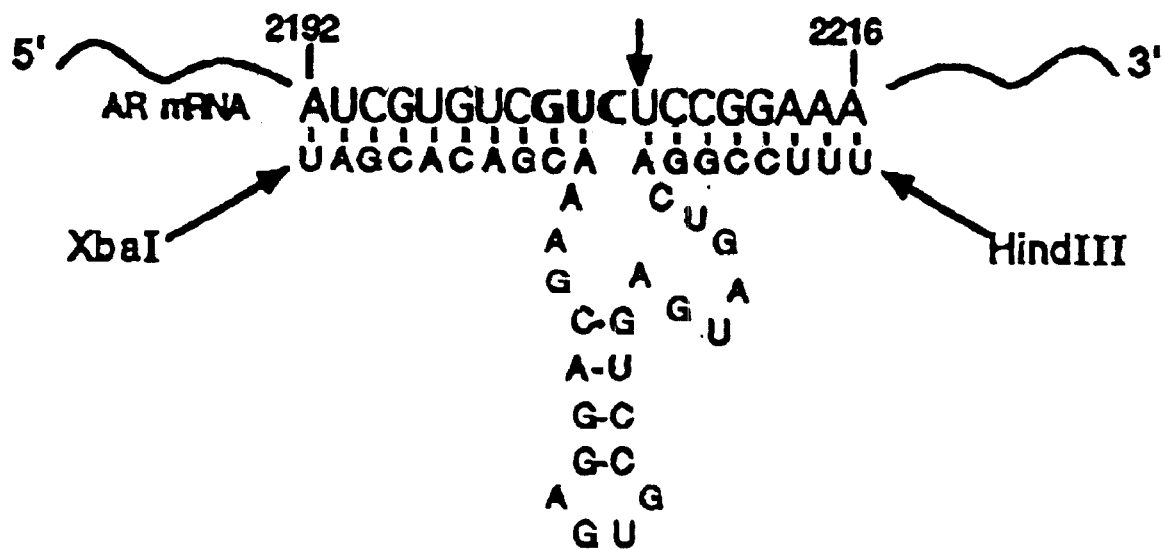
FIG. 16. Rat AR mRNA (SEQ ID NO:10) aligned with ribozyme construct (SEQ ID NO:11). The human counterpart sequences are AR mRNA (SEQ ID NO:1) aligned with ribozyme construct HR2 (SEQ ID NO:2), as shown in Table 1.

Two hammerhead ribozymes, H1 (SEQ ID NO:13) and HR2 (SEQ ID NO:2), cleave human androgen receptor (AR) mRNA at the GUC sequence at positions 1394 and 2375, respectively. In an in vivo assay, both of these hammerhead ribozymes, H1 and HR2, cleave the target AR mRNA substrate into two products at the expected sites. The extent of cleavage varied with the time of incubation, and the molar ratio of ribozyme to substrate. At 30 seconds of incubation at 37° C., HR2 cleaves 37% of the target mRNA at 1:1 molar ratio. Complete cleavage of the target AR mRNA by the two hammerhead ribozymes at 1:1 molar ratio occurs within 30 min. HR2 is more active than H1. A mutant ribozyme (mut-HR2; SEQ ID NO:14) and a oligodeoxynucleotide antisense (antisense HR2 oligo; SEQ ID NO:15) to the target AR mRNA sequence fail to catalyze cleavage of the AR mRNA substrate in vitro. Mut-HR2 has mutations at two bases in the catalytic part (stem II) and the antisense HR2 oligo lacks the catalytic part of HR2 (FIG. 15). The wild-type hammerhead ribozymes, H1 and HR2, the mut-HR2 and the antisense HR2 oligo were cloned into a mammalian expression vector (pCMV) utilizing the RNA polymerase II promoter to create pCMV-H1, pCMV-HR2, pCMV-mut-HR2, and pCMV-anti-HR2, respectively. These constructs were tested for their effects on AR gene expression in culture prostatic cells. Cotransfection of either the H1 or the HR2 expression construct into mammalian cells along with the AR expression plasmid (pCMV-AR) and an AR-responsive reporter plasmid (pMMTV-CAT) results in the inhibition of CAT activity. Both the AR mRNA level and the AR protein level also decline. The extent of the decrease in AR and mRNA is dependent on the level of the expressed hammerhead ribozyme and the decreased AR mRNA also correlates with the extent of inhibition in the CAT activity. However, the $\beta$-actin mRNA level is not affected, indicating that the hammerhead ribozymes H1 and HR2 target specifically the AR mRNA. Similar to the in vitro study, the HR2 ribozyme is more effective than the H1 ribozyme in vivo. The wild-type HR2 ribozyme is much more active in inhibiting AR mRNA expression and CAT activity than the corresponding mutant ribozyme (mut-HR2) and the antisense HR2.

EXAMPLE 2

Expression Vector with Ribozyme Gene

The present example demonstrates that the described synthetic hammerhead ribozymes are designed to cleave specifically AR mRNA within cells, as well as utility therapy in vivo.

The HR2 hammerhead ribozyme was cloned downstream of the rat U6 small nuclear RNA promoter which is transcribed by RNA polymerase III, to give U6-HR2 plasmid. Compared with pCMV-HR2, which is transcribed by pol II, U6-HR2 is more efficient in inhibiting AR mRNA and CAT activity in vivo. A 1:5 molar ratio of pCMV-AR:U6-HR2 achieved 90% reduction of CAT activity, whereas 90% reduction of CAT activity will require a 1:100 molar ratio of pCMV-AR:pCMV-HR2.

EXAMPLE 3

Selection of the Hammerhead Ribozyme Target Sequences in the AR gene

The present example demonstrates the selection of AR mRNA regions targeted by hammerhead ribozymes.

Figure 1:
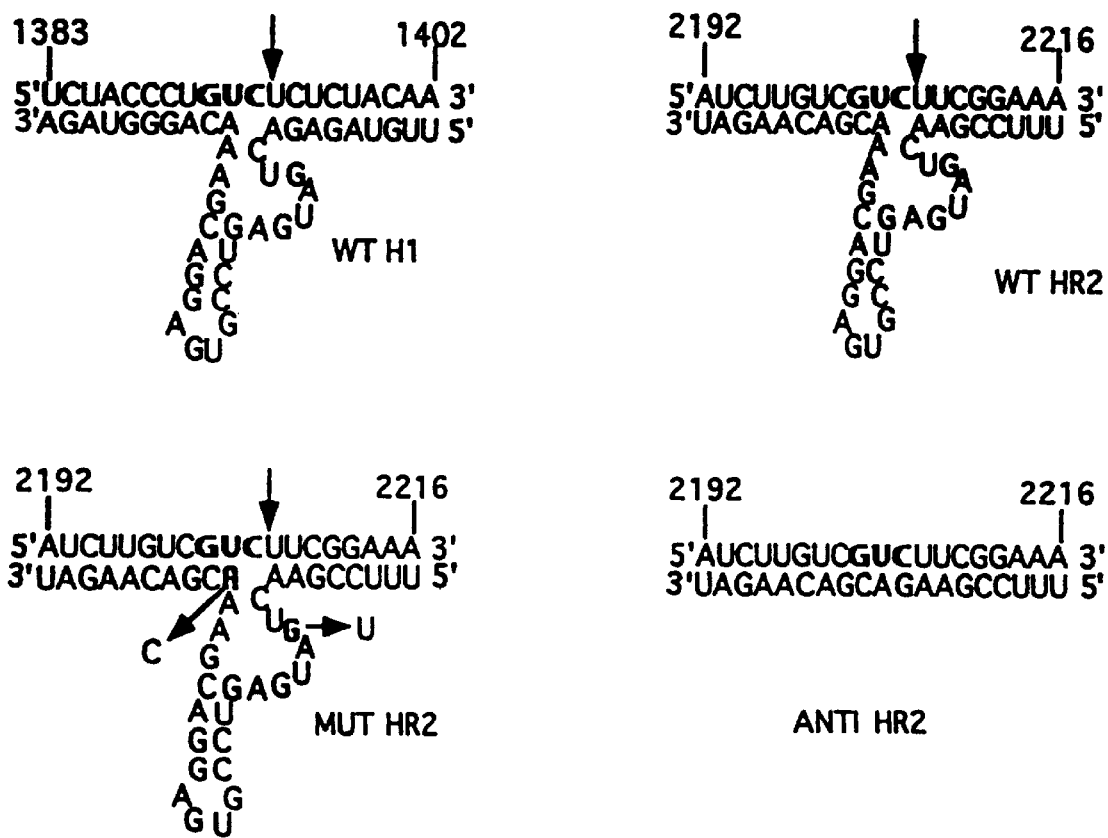
FIG. 1 Structures and positions of wild-type and mutant hammerhead ribozyme elements flanked by antisense oligonucleotide elements complexed to substrates for the GUC sequences found in the coding regions of the human AR mRNA. The numbers at the top of each structure indicate the segment positions of human AR mRNA targeted by hammerhead ribozymes (target for H1 ribozyme is SEQ ID NO:12; target for wild type and mutant HR2 ribozymes and antisense oligonucleotide is SEQ ID NO:1). The arrows show cleavage sites for the ribozymes. WT H1, wild-type H1 hammerhead ribozyme (SEQ ID NO:13). WT HR2, wild-type HR2 hammerhead ribozyme (SEQ ID NO:2). MUT HR2, mutant HR2 hammerhead ribozyme in which 2 bases at the catalytic core sequence were mutated A⇒C and G⇒U (SEQ ID NO:14). ANTI HR2, antisense oligonucleotide HR2 (SEQ ID NO:15).
Figure 2:
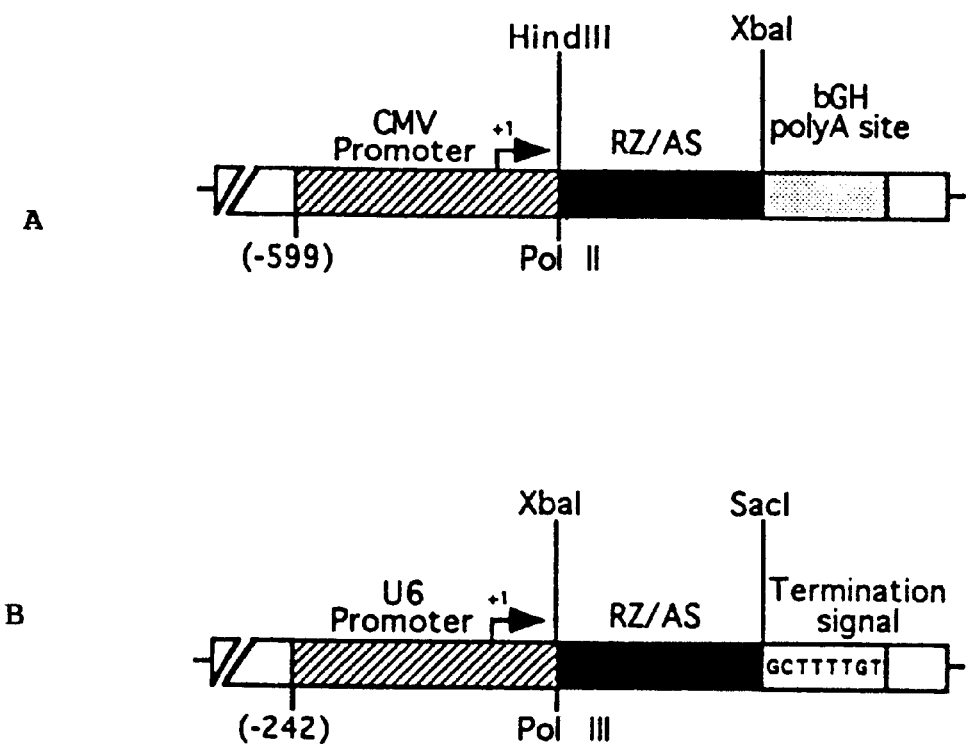
FIGS. 2A and 2B Schematic representation of vector constructs of the hammerhead ribozyme catalytic and antisense oligonucleotide specificity elements.
Figure 3:
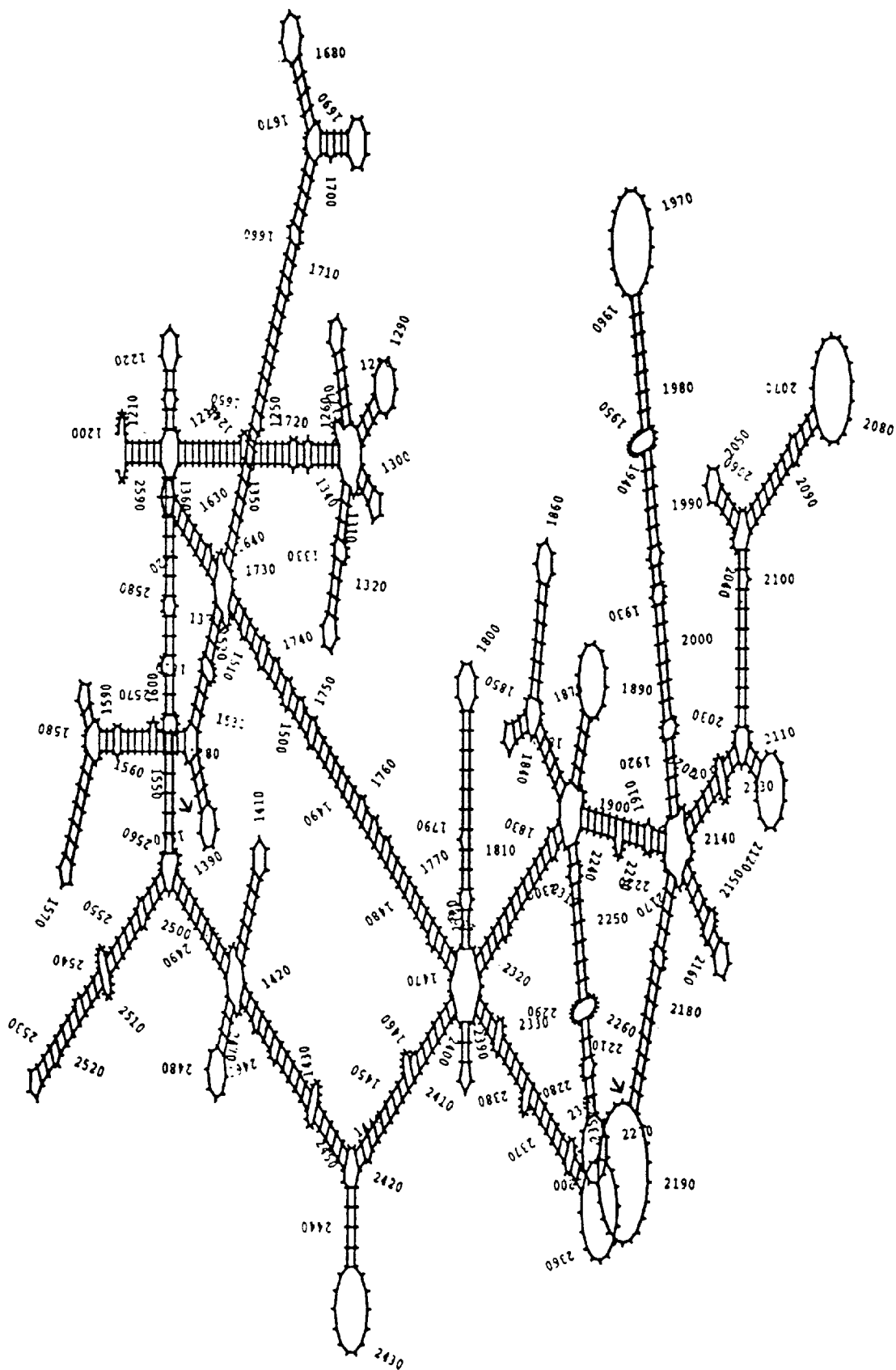
FIG. 3. Secondary structure of the mRNA of the human androgen receptor as determined by the MFOLD program SQUIGGLES. Arrows show the cleavage sites of the androgen receptor mRNA by ribozymes H1 and HR2.

The predicted primary and secondary structures of the entire AR mRNA was searched for open loops that contain the consensus sequence for hammerhead ribozyme cleavage, 5'-HUX-3', which is cleaved 3' of X (X can be A, C or U). RNA substrate with the GUC triplet adjacent to cleavage site was reported to yield very high cleavage efficiency compared with RNA substrate containing other triplet sequences such as CUC, GUA and AUA (Rufner, et al., 1990; Shimayama, et al., 1995; Hendix, et al., 1996). All GUC triplets in the open loop regions were tagged as potential cleavage sites for the hammerhead ribozyme. Then both sides of sequences surrounding these GUC triplets were scanned through the Genbank data base to eliminate sequences with substantial homology to other mRNAs. In order to provide more discrimination and ensue a high rate of cleavage by the hammerhead ribozyme, A/U-rich regions of the flanking sequences (stems I and III) were chosen, because of their generally lesser stability than G/C-rich regions. The greater stability of a G-C base pair diminishes the probability of dissociation of the cleavage products. The presence of A-rich sequences in the flanking sequences of the hammerhead ribozyme also would avoid the possibility of U-G wobble pair formation that would tend to decrease the specificity of the enzyme (Herschlag, et al., 1991; Bertrand, et al., 1994). Two potential target sites were selected within the open reading frame of the AR mRNA to cleave between residues 1393–1394 and between residues 2208–2209. These sites are targeted by ribozymes H1 and HR2, as shown in FIG. 3 in open stem-loop regions of the mRNA. One sequence targeted by H1 consists of 19 residues, 58% A/U-rich. The sequence targeted by HR2 has 18 residues, 61% A/U-rich (FIG. 1).

EXAMPLE 4

Figure 4:
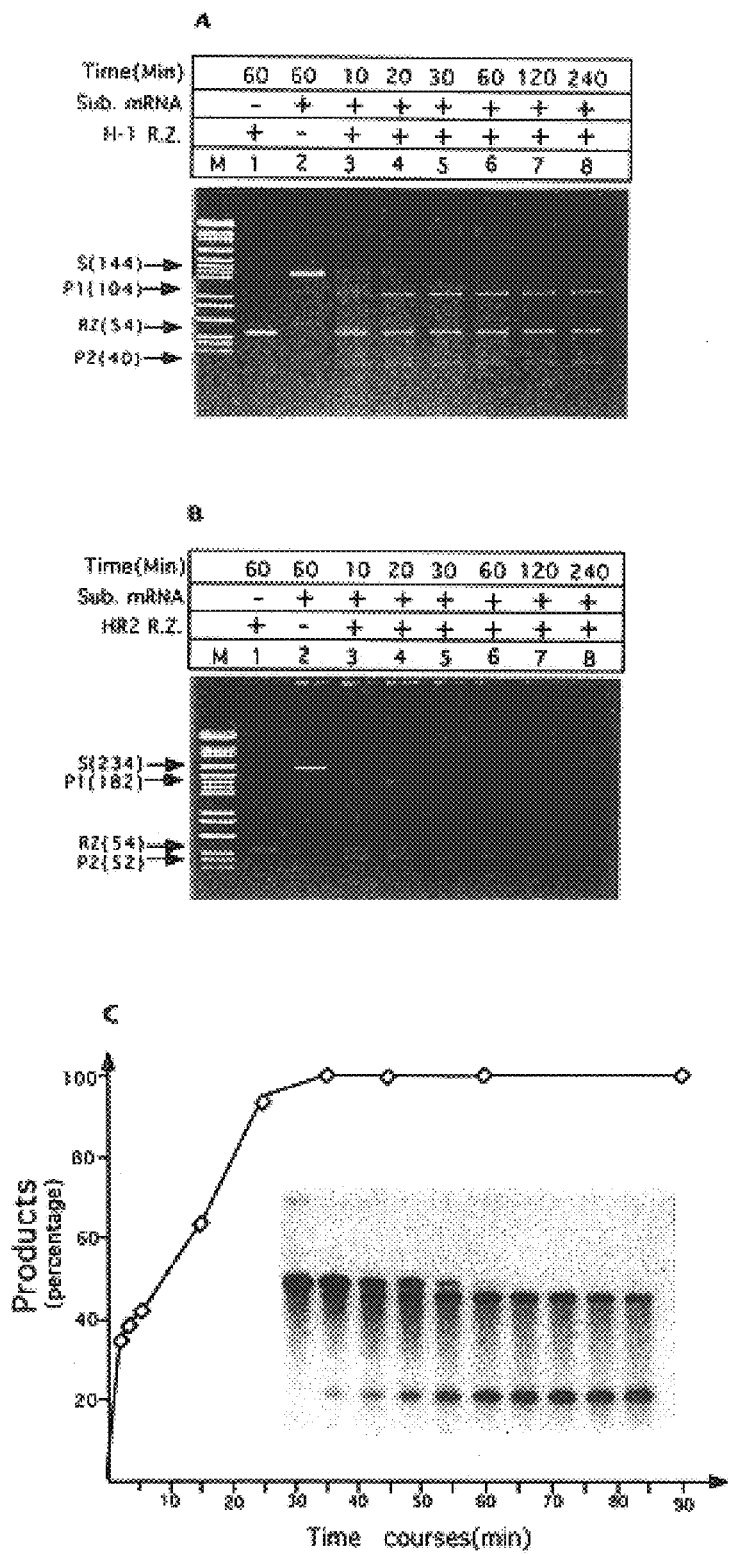
FIGS. 4A, 4B and 4C. Time course of catalytic reactions of the hammerhead ribozyme. Both H1 (SEQ ID NO:13) and HR2 (SEQ ID NO:2) were incubated with the 144 nt and 234 nt of human AR mRNA substrates, respectively. At 1:1 molar ratio of ribozyme:substrate, a reaction mixture containing 10 mM MgCl2, 50 mM Tris-HCI, pH 7.5, 2 mM spermine and 1 mM EDTA, was incubated at 37° C. for 10, 20, 30, 60, 90, 120, and 240 min. The products were loaded onto 10% polyacrylamide/8 M urea gels and separated by electrophoresis. The gels were stained with ethidium bromide. M, size marker. S, mRNA substrate. RZ, hammerhead ribozyme. P1 and P2, catalytic digestion products. A. 0.2 µM of the HI was incubated with 0.2 µM of the 144 nt substrate. B. 0.2 µM of the HR2 was mixed with 0.2 µM of the 234 nt substrate. C. 0.021 µM of unlabeled HR2 was incubated with 0.02 µM of the $^{32}$-p labeled 234 nt substrate at 37° C. for 0.5, 1, 5, 15, 25, 35, 45, 60 and 90 min. The products were separated on a 10% polyacrylamide/8 M urea gel and quantitated using a PhosphorImager.
Figure 5:
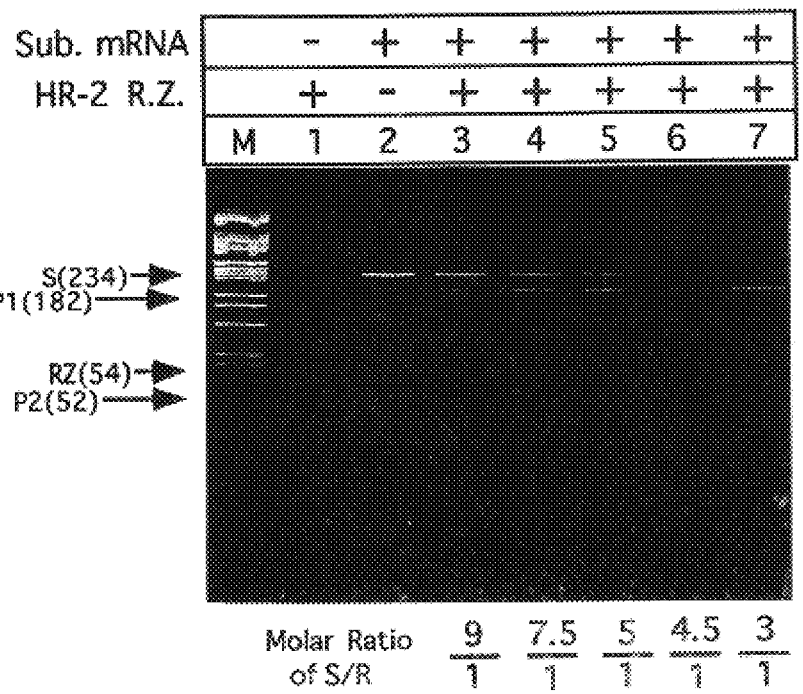
FIG. 5. Catalytic activity of the hammerhead ribozyme at different molar ratios of ribozyme:substrate. The molar ratios of S/R in the reactions are shown at the bottom. Cleavage of the human AR mRNA substrates was demonstrated with decreasing proportions of S/R ratio. After incubation at 37° C. for 30 min, the products were separated by electrophoresis in 10% polyacrylamide/8 M urea gels, and the gels were stained with ethidium bromide. A. HI (SEQ ID NO:13) with 144 nt mRNA substrate. B. HR2 (SEQ ID NO:2) with 234 nt AR mRNA substrate. M, size marker. S, mRNA substrate. RZ or R, hammerhead ribozyme. P1 and P2, digestion products.
Figure 5:
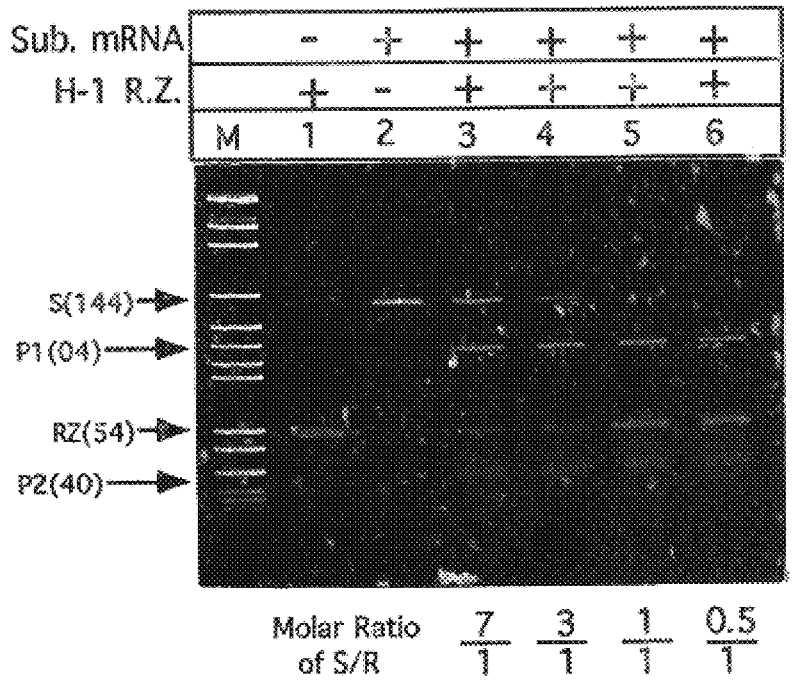

In Vitro Sequence-Specific Catalytic Cleavage of the AR mRNA by the Hammerhead Ribozymes Cleavage reactions of the 144 nt and 234 nt fragments of the AR mRNA substrate by the H1 and HR2 ribozymes in vitro are shown in FIG. 4. Cleavage is dependent on time and the molar ratio of ribozyme:substrate. Using a 1:1 molar ratio of ribozyme:substrate, both ribozymes completely cleave the AR mRNA substrate in less than 30 min, generating the expected products: for H1, a 104 nt and a 40 nt product from the 144 nt AR mRNA substrate (FIG. 4A), and for HR2, a 182 nt and a 52 nt fragment from the 234 nt AR mRNA substrate (FIG. 4B). When $^{32}$P-labeled 234 nt fragment of the AR mRNA and unlabeled HR2 are incubated at a 1:1 molar ratio at 37° C. for different time intervals, 50% of cleavage products are observed at about 13 min (FIG. 4C). On the other hand, when different ratios of the ribozyme and substrate are mixed, complete cleavage of the 234 nt fragment of the AR mRNA is observed using a 1:3 molar ratio of HR2:AR mRNA substrate in 30 min at 37° C. (FIG. 5A). By contrast, complete cleavage of the 144 nt fragment requires a 1:1 molar ratio of H1: substrate in the same time (FIG. 5B). The results show that HR2 is more active than is H1.

Figure 6:
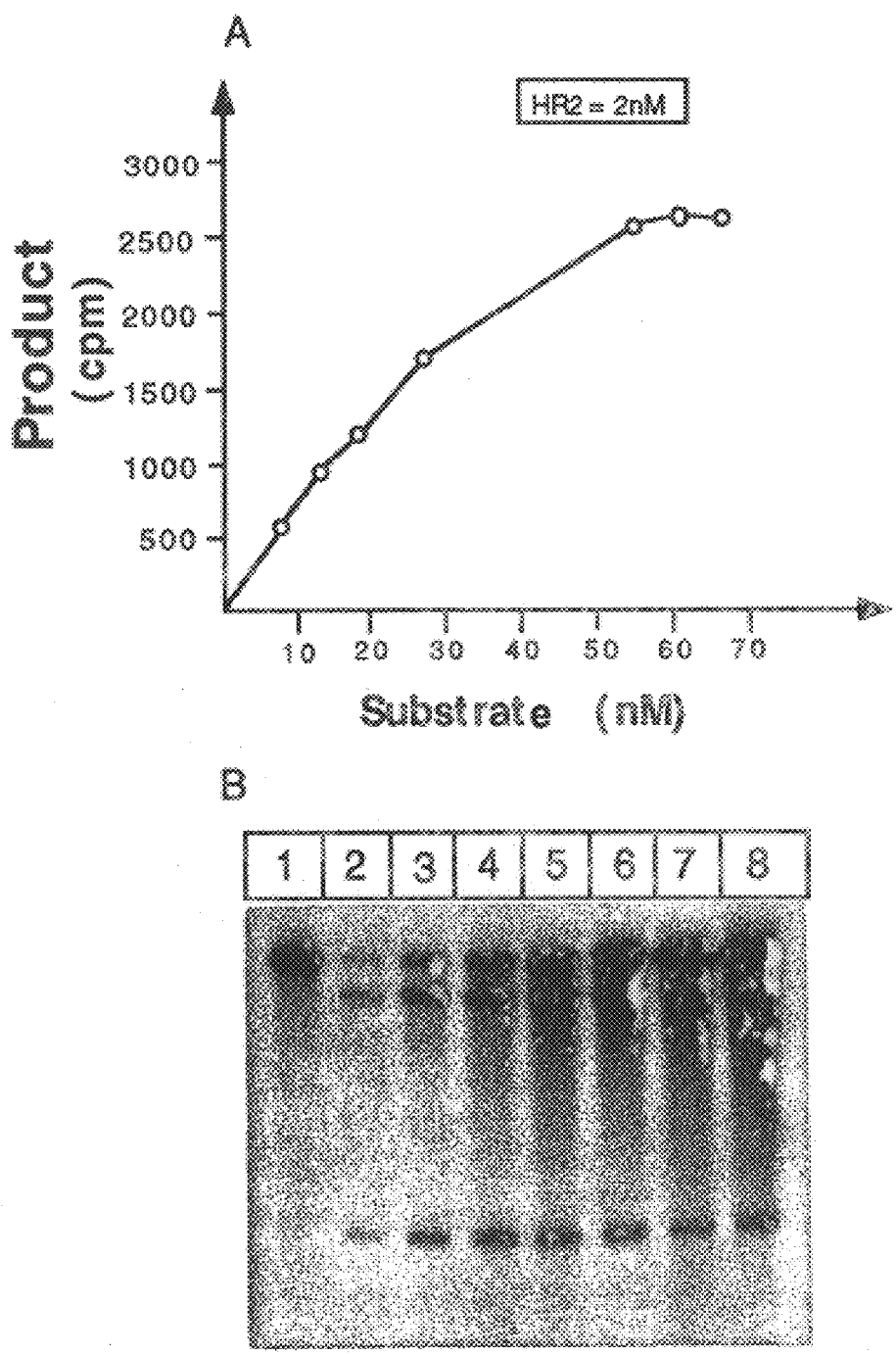
FIG. 6. Steady-state kinetics of the HR2 hammerhead ribozyme reaction. The reaction shown was carried out with 2 nM of cold HR2 (SEQ ID NO:2) with different concentrations of the $^{32}$P labeled 234 nt human AR mRNA substrate: 8 nM (lane 2), 14 nM (lane 3), 20 nM (lane 4), 30 nM (lane 5), 57 nM (lane 6), 60 nM (lane 7) and 65 nM (lane 8). Reaction was at 37° C. for 40 min. Lane 1. mRNA substrate only.

Steady-state cleavage velocities were measured for 2 nM of HR2 with mRNA substrate concentrations ranging from 8 to 70 nM. When the different concentrations of $^{32}$P-labeled 234 nt substrate were incubated with cold HR2, the ribozyme was effectively saturated with substrate at high concentrations. Under the reaction conditions at 37° C. in 10 mM MgCl2/50 mM Tris-HCl, pH 7.5/2 mM spermine/1 mM EDTA for 40 min, HR2 ribozyme cleaved more products of the RNA substrate with increasing the RNA substrate concentrations (FIG. 6). In vitro cleaved the 234 nt substrate with high efficiency.

Figure 7:
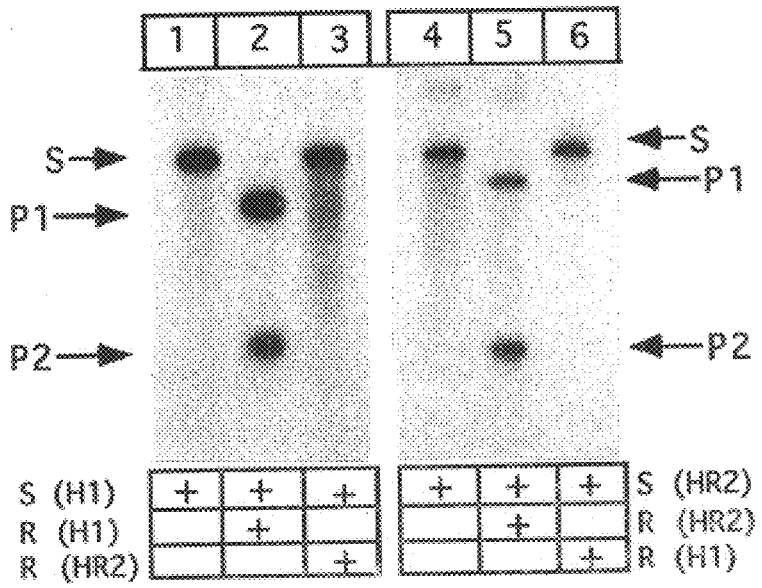
FIGS. 7A and 7B. Target-specific cleavage by the hammerhead ribozyme. A. $^{32}$P-labeled 144 nt and 234 nt fragments of the human AR mRNA substrates were incubated with unlabeled H1 (SEQ ID NO:13) and HR2 (SEQ ID NO:2), respectively, at a 1:1 molar ratio (0.2 µM each) at 37° C. for 60 min in 10 mM MgCl$_2$,50 mM Tris-HCI, pH 7.5, 2 mM spermine, 1 mM EDTA. Lane 1. 144 nt mRNA substrate only. Lane 2. 144 nt mRNA substrate plus H1. Lane 3. 144 nt mRNA substrate plus HR2. Lane 4. 234 nt mRNA substrate only. Lane 5. 234 nt mRNA substrate plus HR2. Lane 6. 234 nt mRNA substrate plus H1. S. mRNA substrate. P1 and P2. digestion products. B. Inactivation of HR2 by point mutations. The 234 nt AR mRNA substrate was mixed either with HR2 (SEQ ID NO:2), or mut-HR2 (SEQ ID NO:14), or antisense oligo HR2 (SEQ ID NO:15) (see FIG. 3) at 37° C. for 60 and 120 min. Products were separated on a 10% polyacrylamide/8M urea gel; then the gel was stained with ethidium bromide. M. size marker. Lane 1. antisense oligonucleotide only. Lane 2. HR2 only. Lane 3. mutant HR2 only. Lane 4. 234 nt AR mRNA substrate only. Lanes 5 and 8. 234 nt mRNA substrate with antisense oligo HR2. Lanes 6 and 9. 234 nt mRNA substrate with HR2. Lanes 7 and 10. 234 nt mRNA substrate with mutant HR2. Sub. mRNA substrate. Mut. mutant HR2 (SEQ ID NO:14). WT. wild type HR2 (SEQ ID NO:2). AS. antisense oligo HR2 (SEQ ID NO:15).
Figure 7:
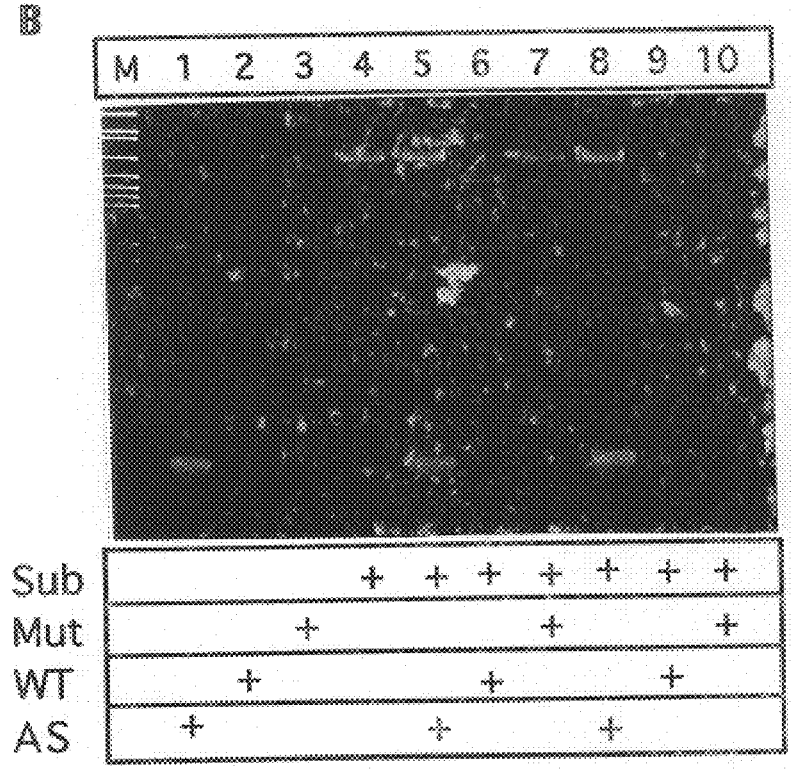

That these hammerhead ribozymes specifically recognize their target sequences was demonstrated by the fact that HR2 was totally ineffective in catalyzing the cleavage of the AR mRNA substrate for H1 (FIG. 7A, lane 3), and vice versa (FIG. 7A, lane 6). Point mutations (A➔C and G➔U) in the catalytic domain of HR2 (FIG. 1) resulted in complete loss of the catalytic activity in vitro (FIG. 7B, lanes 7,10). The specificity elements of HR2 by antisense HR2 deoxyoligo also failed to cleave the 234 nt AR mRNA substrate (FIG. 7B, lanes 5, 8). The mutant HR2 hammerhead ribozyme construct, pCMV-mut-HR2, was tested in transfection studies to distinguish the antisense effect from the enzymatic activity on the AR mRNA substrate.

EXAMPLE 5

Efficiency and Specificity of the Hammerhead Ribozyme in Transient Contransfection Assays Toward the Target AR mRNA in Cell Culture In order to demonstrate the efficiency of H1 and HR2 inactivation of AR gene expression at the cellular level, H1 and HR2 ribozymes, mutant ribozyme (mut-HR2) and the antisense oligo HR2 alone (without the catalytic loop) were cloned into a mammalian expression vector (pCMV) and transfected them into PC-3 cells with the target vector (pCMV-AR) and the reporter vector (pMMTV-CAT). An analysis of the expression of pMMTV-CAT showed that CAT activity was inhibited with increasing doses of hammerhead ribozyme transfected in the form of pCMV-H1 and pCMV-HR2. At 1:20, 1:50 and 1:100 molar ratios of target:H1 ribozyme, CAT activity was reduced by 10%, 55% and 80%, respectively, relative to that transfected with the control vector (FIG. 8A). Also, CAT activity was reduced by 60%, 75% and 95%, respectively, at the same molar ratios of the target/HR2 ribozyme (FIG. 8B). These results demonstrate the efficacy of the transfected ribozyme in cultured cells.

Figure 9:
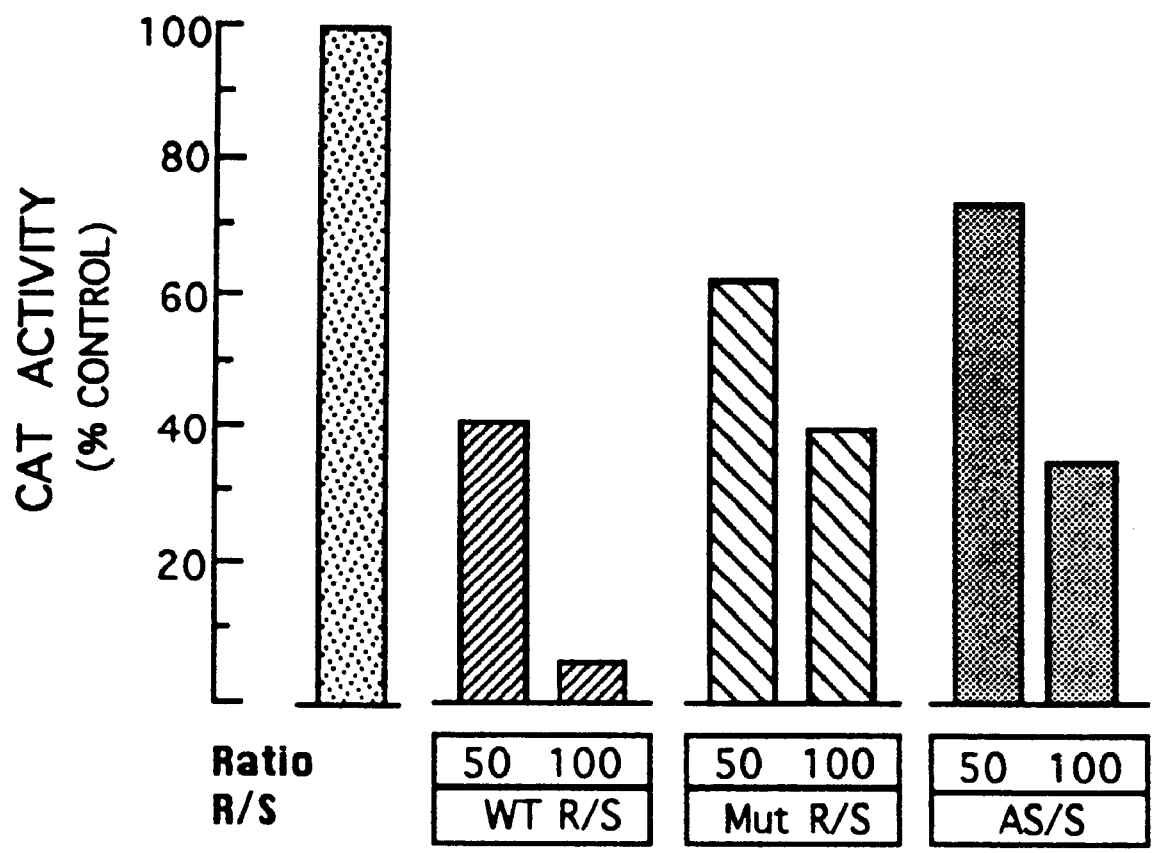
FIG. 9. Inhibition of CAT gene expression in the presence of wild-type ribozyme and mut HR2 ribozyme as well as antisense oligo HR2 vectors in transiently transfected PC-3 cells. The target vector (pCMV-AR) and the reporter vector (pMMTV-CAT) were transfected into the PC-3 cells with either pCMV-HR2, or pCMV-mut-HR2, or pCMV-anti-HR2, or pCMV control vector. Molar ratio is shown at the bottom. Total DNA concentration was normalized to 10 µg with the pCMV control vector. After 48 hours, cells were harvested and assayed for CAT activity. Results are expressed relative to the control vector. S. The target vector (pCMV-AR). R. wild-type or mutant ribozyme or antisense oligo vector. WT R. wild-type ribozyme HR2 (SEQ ID NO:2). Mut R. mutant ribozyme HR2 (SEQ ID NO:14). AS. antisense oligo HR2 (SEQ ID NO:15).

To assess catalytic activity versus antisense effect of the ribozyme on inactivating AR gene expression, wild-type HR2 (pCMV-HR2) with mutant HR2 were compared, which lacks catalytic activity (FIG. 7B, lanes 7,10) and antisense RNA HR2 (pCMV-anti-HR2). The mutant ribozyme and antisense RNA had inhibitory effects, but much smaller than with wild-type HR2. At 1:50 and 1:100 molar ratios of substrate to ribozyme or antisense RNA, wild-type HR2 inhibited 6% and 95% of the CAT activity, respectively, while the mutant ribozyme inhibited 37% and 60%, respectively, and the antisense RNA only 20% and 65%, respectively (FIG. 9). These results showed that inhibition of the CAT activity is due mainly to the catalytic property of the hammerhead ribozyme, not to antisense effect.

Figure 10:
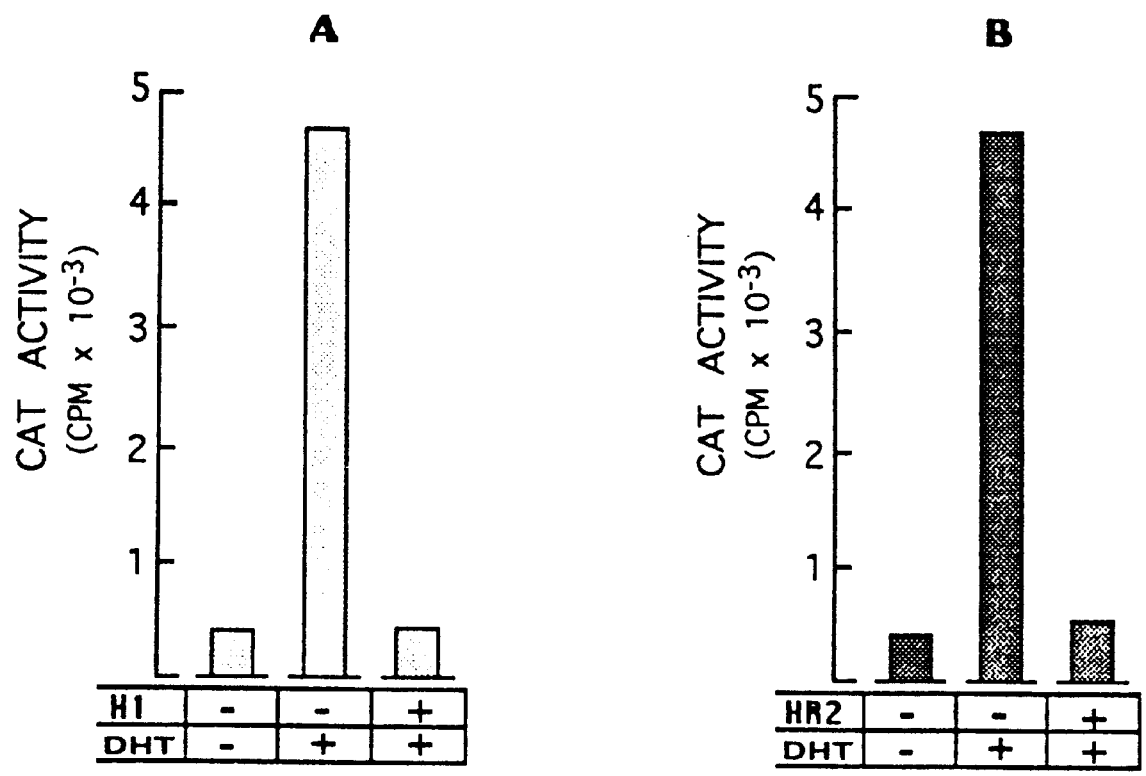
FIGS. 10A and 10B. Inhibition of androgen response by the hammerhead ribozyme in CV-1 cells stably transfected with rat AR (CV-1/AR). Stably transfected CV-1 cells expressing AR were transfected with 3.5 μg of each of the reporter vector (pMMTV-CAT), H1 or HR2 or pCMV control vector. Cells were cultured in the absence or presence of $10^{-8}$ M DHT. After 24 hours, cell extracts were assayed for CAT. H1. H1 ribozyme. HR2. HR2 ribozyme. DHT. dihydrotestosterone. A, CV-1/AR cells transfected with the H1 ribozyme. B, CV-1/AR cells transfected with the HR2 ribozyme.

The vector containing the AR cDNA was transfected into CV-1 cells that were derived from monkey kidney tumor cells. Positive clones expressing AR mRNA were screened by RT-PCR. A CV-1 clone with stably expressing AR mRNA (CV-1/AR) was transfected with pMMTV-CAT in the presence of $10^{-8}$ MDHT or absence of DHT. Chloramphenicol acetyl transferase activity was induced nine-fold by DHT (FIG. 10). When CV-1/AR cells were cotransfected with pMMTV-CAT and either pCMV control vector, or pCMV-H1, or pCMV-HR2 and cultured in the presence of DHT, CAT activity of the cells transfected with the ribozyme was nine-fold lower than that of the cells cotransfected with the control vector (FIG. 10). The AR hammerhead ribozymes can be concluded to inactivate the AR mRNA expression with high specificity and efficiency.

It has been observed that a hammerhead ribozyme whose expression is under the control of an RNA pol III promoter is more effective in inhibiting target gene expression as compared to one whose expression is under the control of an RNA pol II promoter (Cotton and Brinstiel, 1989; Yu et al., 1993; Michienzi et al., 1996; Perriman et al., 1996). To determine if this could more efficiently inhibit AR mRNA expression, HR2 wild-type, mutant ribozyme and antisense oligo were subcloned downstream of the rat U6 small nuclear gene promoter which is driven by the RNA pol III, to yield U6-HR2, U6-mut-HR2 and U6-anti-HR2 constructs.

Figure 8:
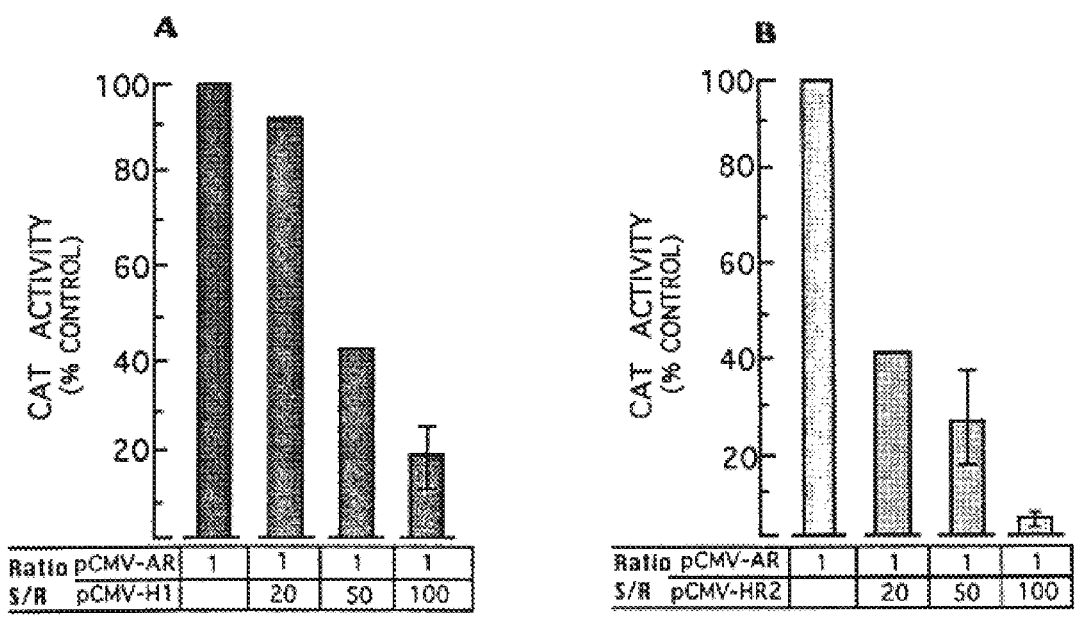
FIGS. 8A and 8B. Effect of the hammerhead ribozyme on CAT activity in transiently transfected PC-3 cells. The target vector (pCMV-AR) and the reporter vector (pMMTV-CAT) were cotransfected into PC-3 cells with H1 or HR2 or pCMV control vector at molar ratios of 1:20, 1:50 and 1:100 (target vector/hammerhead ribozyme). Tested DNA concentration was normalized to 10 µg with pCMV control vector. At 48 hours post transfection, the cells were harvested and CAT was assayed. The values are presented as relative percentage. The molar ratios of Hi or HR2 to the AR expression vector are shown at the bottom.

The pCMV-AR and pMMTV-CAT, along with either U6-HR2, or U6-mut-HR2, or U6-anti-HR2 or U6 control vector were transfected into NIH3T3 cells by the calcium phosphate method (Chan et al., 1995). For comparison, pCMV-HR2 was used in parallel (FIG. 8). The data showed that U6-HR2 was more effective in inhibiting CAT activity in NIH3T3 cells (FIG. 11). At a 1:5 molar ratio of pCMV-AR:U6-HR2, CAT activity was reduced by about 90% (FIG. 11), whereas the same reduction in CAT activity in the case of the pCMV-HR2 required a 1:100 molar ratio of the pCMV-AR:pCMV-HR2 (FIG. 8). In agreement with the findings of Yu et al. (1993), the ribozyme under the control of the RNA pol III promoter exhibits stronger inactivation of gene expression than under the control of the RNA pol 11 promoter (Yu et al., 1993). The mutant ribozyme and anti sense RNA yielded less than 20% of inhibition of CAT activity at the same molar ratio (FIG. 11, lanes 4, 5).

EXAMPLE 6

The present example demonstrates that the decrease in CAT activity results directly from a decrease in AR mRNA due to the action of the ribozyme.

Total RNAs were isolated from the PC-3 cells transfected with the AR cDNA expression vector and either pCMV-HR2, or pCMV-mut-HR2 or pCMV-anti-HR2 at 1:25, 1:50 or 1:100 molar ratios. The RNase protection assays were performed using an antisense AR RNA probe that spans the expected cleavage site of the AR mRNA and analyzed the AR mRNA levels in different treatments of the PC-3 cells.

Figure 12:
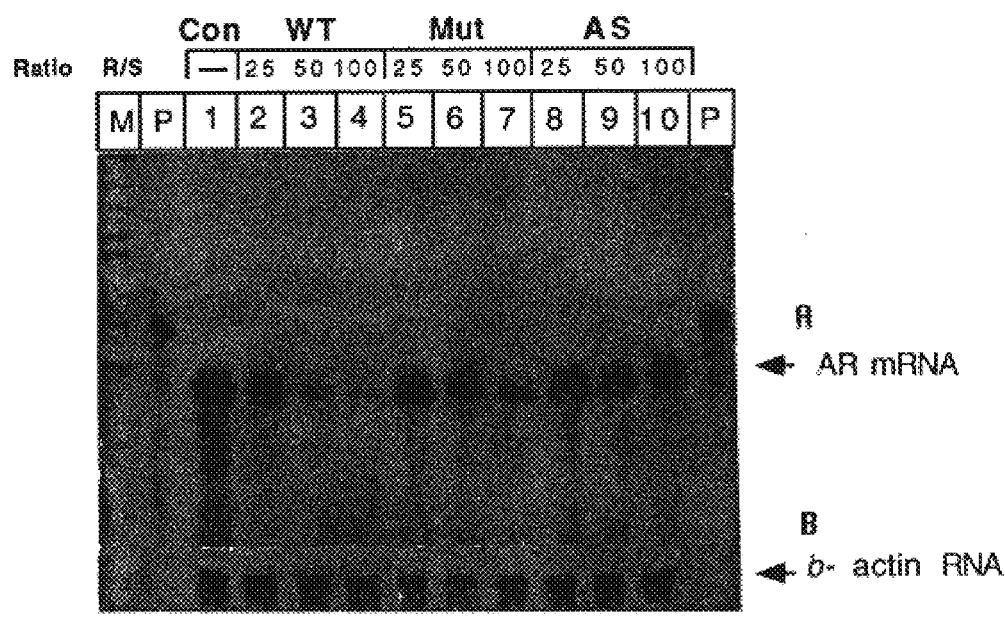
Figure 12:
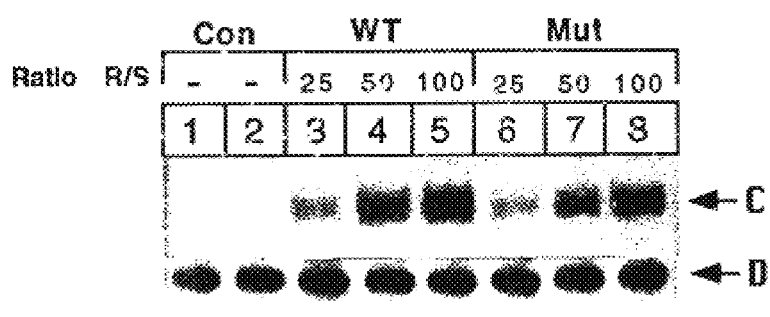
Figure 13:
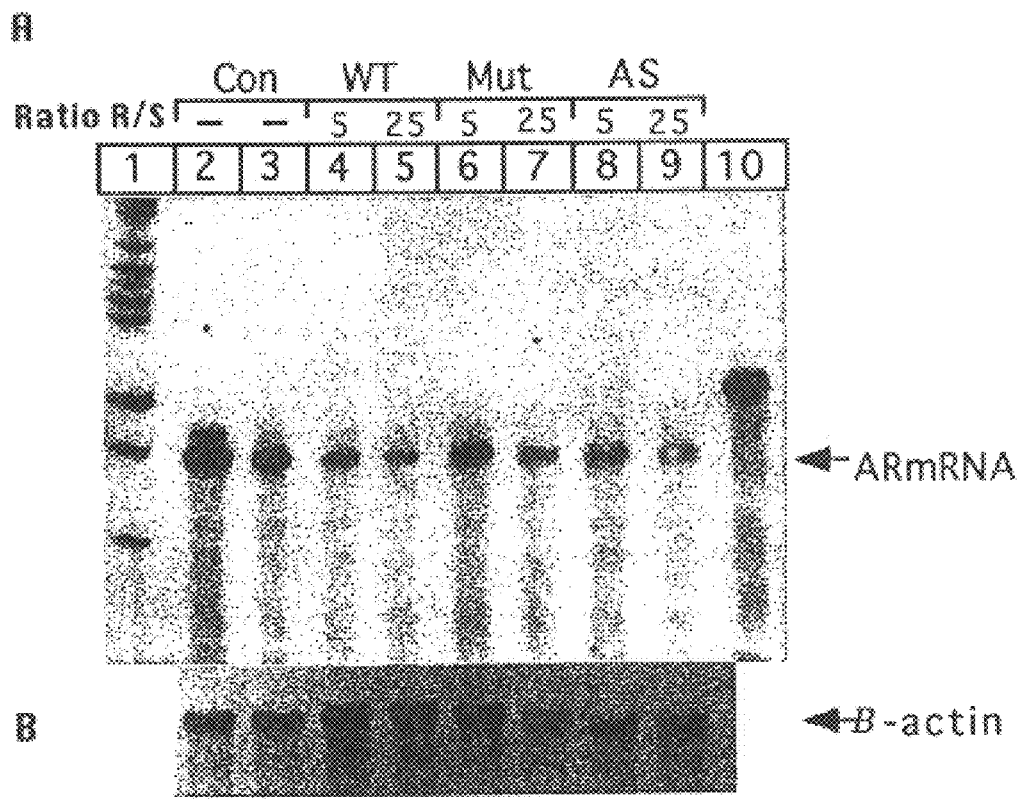
FIG. 13. RNA polymerase III promoter-driven expression of hammerhead ribozyme and the ribozyme mediated reduction of the AR mRNA in transfected cells. The PC-3 cells were cotransfected with pCMV-AR and either U6-HR2, or U6-mut-HR2, or U6-anti-HR2, or U6 control vector at 1:5 or 1:25 molar ratio. After 12 hours, total RNA was extracted. RNase protection assay was performed as described in materials and methods. $10^{'6}$ cpm of the 179 nt fragment of anti AR mRNA probe (13A) and $10^5$ cpm of the 638 nt fragment of anti β-actin mRNA probe (13B) were hybridized with 8 and 1μ of total RNA from transfected cells. Protected RNA was analyzed on 5% polyacrylamide/8 M urea gels and exposed to X-ray film for 3 days (13A) and 1 day (13B). Lane 1, size marker. Lanes 2 and 3; PC-3 cells transfected with 1 μg of pCMV-AR only. Lanes 4 and 5; PC-3 cells cotransfected with 1 μg of pCMV-AR and 5 μg or 25 μg of U6-HR2. Lanes 6 and 7; PC-3 cells cotransfected with 1 μg of pCMV-AR and 5 μg or 25 μg of U6-mut-HR2. Lanes 8 and 9; PC-3 cells cotransfected with 1 μg of pCMV-AR and 5 μg or 25 μg of U6-anti-HR2. Lane 10, antisense RNA probe only. S. the AR expression vector. R. wild-type or mutant U6 hammerhead ribozyme or antisense oligo vector. Con. PCMV-AR vector only. WT. Wildtype of U6-HR2. Mut U6-mut-HR2. AS. U6-anti-HR2.
Figure 14:
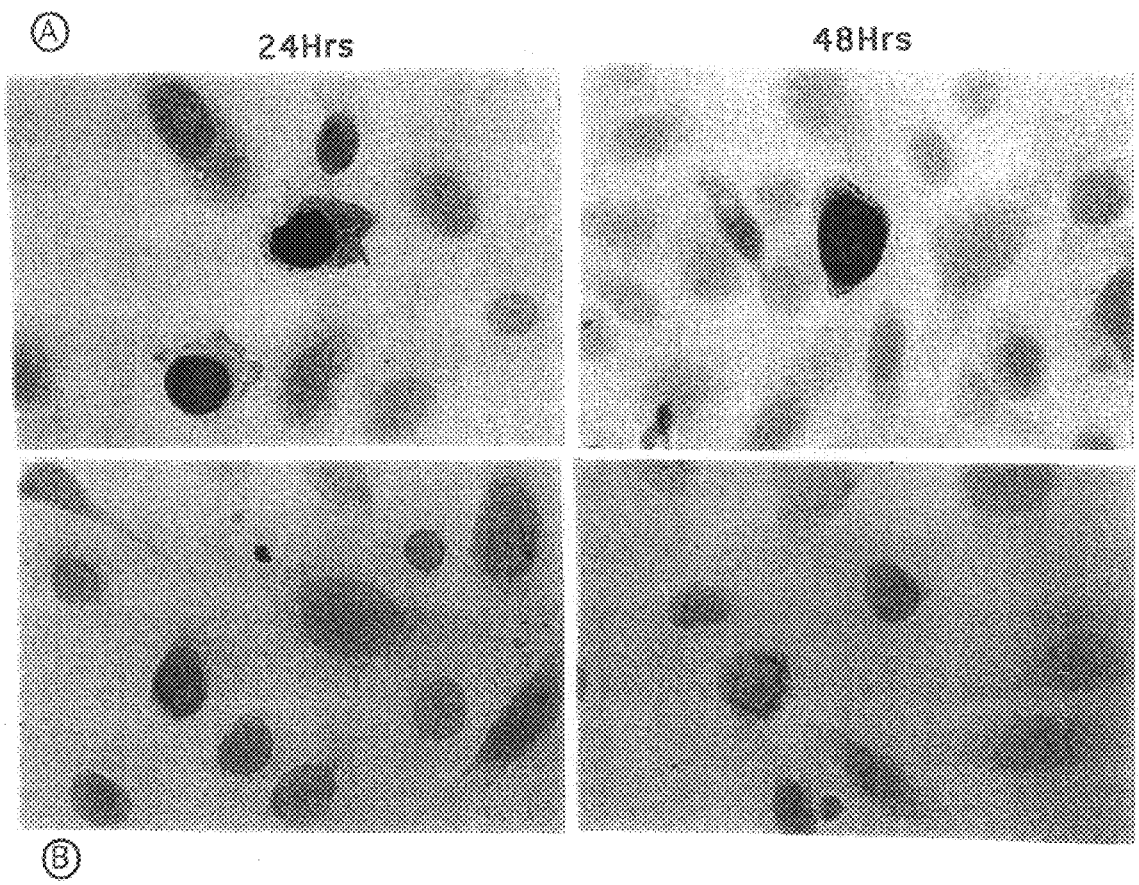
FIGS. 14A and 14B. Immunocytochemical staining of the androgen receptor In the PC-3 cells transfected with the hammerhead ribozyme. PC-3 cells were transfected with 0.2 μg of the AR expression vector and 20 μg of pCMV control vector or 20 μg of the HR2 hammerhead ribozyme vector. After 24 and 48 hours, the cells were fixed, and incubated with AR antibody. 14A. PC-3 cells transfected with the AR expression vector. The positive immunostaining of AR is observed in the nuclei. 14B. PC-3 cells transfected with AR expression vector and HR2 hammerhead ribozyme. The AR immunostaining is weak and mainly located in the cytoplasm.

The results shown in FIGS. 12A, B and C indicate that AR mRNA normalized to the amount of the control β-actin mRNA in each sample was lower in cells transfected with hammerhead ribozyme. Wild-type HR2 more efficiently inhibited AR mRNA at different molar ratios of the pCMV-AR:pCMV-HR2 than the control, and was more effective in inhibiting AR mRNA expression than the mutant ribozyme and antisense RNA. When different concentrations of wild-type and the mutant HR2 were transfected into PC-3 cells, the levels of ribozyme expression were detected by quantitative RT-PCR, using specific primers from the stem I sequences of the HR2 ribozyme (FIG. 12C). Taken together, these results show that the inhibitory activity is dependent on the level of ribozyme expression in cultured cells. In order to further study the effects of the ribozyme transcribed by RNA pol III on inhibition of AR mRNA expression, pCMV-AR expression vector was transfected into PC-3 cells with either U6-HR, or U6-mut-HR, or U6-anti-HR2, or U6 control vector at 1:5 and 1:25 molar ratios. Ribonuclease protection assays were performed to analyze AR mRNA levels in different transfected cells. Results as shown in FIG. 13 demonstrate that the wild-type ribozyme is not only more active in inhibiting the target AR mRNA than the mutant ribozyme and antisense RNA, but also more effective than HR2 which is transcribed by the RNA pol 11 (compare FIG. 12 with FIG. 13). The decrease in AR mRNA by the ribozyme correlates with the decrease in CAT activity. However, the products resulting from the cleavage of the AR mRNA by the ribozyme. Were not detected. These cleavage products may be degraded too quickly to be detected (Cofton and Bimstiel, 1989; Yuan et al., 1992; Sullenger and Cech, 1993; Xing and Whitton, 1993; Lieber and Strauss, 1996).

EXAMPLE 7

In this study, it was shown that the proximal 5' flanking promoter region of the AR gene lacks obvious TATA or CAAT boxes, but contains a pur/pyr-rich region. This region is conserved in human, rat and mouse species.

In the rat, six copies of the GGGGA repeat sequence from position −123 to −94 are located immediately upstream of the GC-rich box which is bound by Sp1 nuclear transcription factor. In recent studies, it has been demonstrated that the pur/pyr-rich region can form a non-B DNA conformation and plays an important role in a number of TATA-less gene promoters such as the promoter for the epidermal growth factor receptor, human Ha-ras, human c-myc genes and others (Cooney et al., 1988; Hoffman et al., 1990; Grigoriew et al., 1992; Roy, 1993; Mayfield et al., 1994; Mouscadat et al., 1994). The present invention provides evidence that the pur/pyr-rich region of the AR gene can form a non-B DNA conformation that is sensitive to the single-strand specific S1 nuclease. Fine mapping analysis reveals that both DNA strands of the pur/pyr-rich region are cleaved by S1 nuclease and form an asymmetric cleavage pattern. Further studies show that the pur/pyr-rich region forms a triple helical H-form DNA conformation. This pur/pyr-rich region can be bound by antiparallel and parallel purine rich oligonucleotides, but not by pyrimidine-rich TFOs or random DNA sequences under physiological conditions. Gel mobility shift assays and DNase I footprinting studies show that the pur/pyr-rich region binds a novel pyrimidine single-strand DNA binding protein and also a double-strand DNA binding protein, the nuclear transcription factor Sp1. Mutation of the region showed that the pur/pyr-rich region serves as an enhancer element and indicates an important regulatory element of AR gene expression.

The novel pyrimidine-single-stranded DNA binding protein will be cloned to determine how the protein regulates the AR gene transcription. Also, the relationship between the single-stranded DNA binding protein and nuclear transcription factor Sp1 in the pur/pyr-rich region will be investigated. In addition, TFOs will be designed to study its effect on AR gene expression.

EXAMPLE 8

In the present study, two hammerhead ribozymes were designed to target specific GUC specimens in AR mRNA.

In a cell-free system, both hammerhead ribozymes can cleave AR mRNA at the expected sites, but the mutant hammerhead ribozyme and antisense oligonucleotide do not cleave the target mRNA sequences. At 1:1 molar ratio of substrate:hammerhead ribozyme, both hammerhead ribozymes cleave the mRNAs completely within 30 min at 37° C. The hammerhead ribozyme recognizes only its target sequences, and catalyzes the cleavage of the mRNA substrates, indicating its specificity and efficiency. The hammerhead ribozyme can cleave the AR mRNA in cultured cells. This effect is due to the endonuclease activity rather than to the antisense effect. Compared to the HI hammerhead ribozyme, the HR2 hammerhead ribozyme is more effective in vitro and in vivo. The HR2 hammerhead ribozyme driven by the RNA pol III promoter is more powerful than the one driven by the RNA pol II promoter.

Transgenic mice expressing hammerhead ribozyme have been created (Efrat et al., 1994; Larsson et al., 1994; L'Huillier et al., 1996). The hammerhead ribozyme inhibits target gene expression to different levels in such mice. In order to detect whether ribozyme can inhibit endogenous AR mRNA in cells. LNCaP cells derived from human prostate cancer cells were chosen. It produces endogenous AR mRNA and prostate specific antigen (PSA). PSA expression is dependent on androgen and AR. When HR2 ribozyme expression vector was transfected into LNCaP cells, PSA activity was analyzed 48 hour post-transfection. Results showed that the ribozyme inhibit 50% of PSA activity compared to the control group. In further studies, transgenic mice expressing hammerhead ribozyme targeting the AR gene will be generated. The hammerhead ribozyme will be cloned downstream of the rat probasin promoter that is specific for prostate tissue (Greenberg et al., 1994). Hammerhead ribozyme expression by RT-PCR in transgenic mice will be detected. Transgenic mice expressing the hammerhead ribozyme will be selected. To examine AR gene and hammerhead ribozyme expression in prostate glands, histological studies of the prostate gland in the transgenic mice will also be conducted. AR regulates the development of the male reproductive organs.

EXAMPLE 9

Function of Hammerhead Ribozyme

A hammerhead ribozyme contains antisense sequence to the target substrate. For this reason, it is important to establish whether this type of ribozyme truly functions as a catalytic RNA endonuclease or whether the "activity" is due instead to an antisense effect in cultured cells. A wild-type hammerhead ribozyme and a mutant one with substitutions in the catalytic core were designed. The mutant hammerhead ribozyme (mut-HR2) and the antisense oligo (antisense HR2) do not cleave the target RNA substrate in vitro (FIG. 7B). The wild-type, mutant hammerhead ribozymes and the antisense RNA oligo in vivo were further examined. It was found that both the mutant hammerhead ribozyme and the antisense RNA oligo have inhibitory effects on AR mRNA expression and CAT activity, but the wild-type hammerhead ribozyme is much more inhibitory than the antisense oligo and/or the mutant hammerhead ribozyme (FIGS. 9 and 11). It was further shown that the hammerhead ribozyme action is due to endonuclease activity rather than to an antisense effect (Scanlon et al., 1991; Ojwang et al., 1992; Lange et al., 1993; Inokuchi et al., 1994). The levels of AR mRNA and the CAT activities in transfected cells suggested that the expression of AR mRNA is inversely correlated with the expression of hammerhead ribozyme. With increasing amounts of transfected hammerhead ribozyme, AR gene expression is further suppressed. To achieve a higher effect of hammerhead ribozyme on its substrate, it must be used in excess and properly localized.

A promoter driving a hammerhead ribozyme must be much stronger than a promoter generating a target RNA substrate. Compared with the ribozyme transcribed by the RNA pol III, a higher dose of the ribozyme transcribed by the RNA pol II is required to achieve the same degree of inhibition. It is known that the yield of RNA transcribed by the RNA pol II is lower in cell systems than that transcribed by the RNA pol III (Brafty et al., 1993; Bertrand et al., 1994; Chowrira et al., 1994). The RNA pol II system is usually employed for mRNA transcription or expression of a long antisense RNA. This system generates the cap and poly A structures that are required for the stability of RNA in vivo. However, RNA pol II is not suitable for production of short RNA molecules (Sanfacon and Hohn, 1990). In contrast, RNA pol III produces small RNAs at a higher rate of transcription and in various tissues (Coften and Brinstiel, 1989; Perriman et al., 1996). Using RNA pol III, it is possible to generate a short hammerhead ribozyme in cells with a stable secondary structure that protects the hammerhead ribozyme from nuclease attack (Perriman et al., 1996). It has been reported that a hammerhead ribozyme driven by the RNA pol III promoter in a cell culture system can reduce target gene expression to a greater extent than a hammerhead ribozyme driven by the RNA pol II promoter (Cotten and Brinstiel, 1989; Yu et al., 1993; Thompson et al., 1996).

Studies were conducted to compare the ability of the hammerhead ribozyme transcribed by RNA pol II and by RNA pol III promoters to inhibit AR mRNA expression in cultured cells were undertook. The HR2 ribozyme was cloned into expression vectors with either a RNA pol II promoter (pCMV-HR2) or a RNA pol III promoter (U6-HR2). It was found that the U6-HR2 driven by RNA pol III dramatically inhibits AR mRNA level and CAT activity (FIGS. 11 AND 13). The CAT activity and AR mRNA are reduced by about 90% and 70%, respectively, at a 1:5 molar ratio of the target vector (pCMV-AR): ribozyme (U6-HR2). Similar inhibition of AR expression and CAT activity by the HR2 ribozyme driven by RNA pol II promoter requires a 1:100 molar ratio of target vector (pCMV-AR): hammerhead ribozyme (pCMV-HR2) (FIGS. 8 and 12). This demonstrates that the RNA pol III promoter. more efficiently promotes transcription of the hammerhead ribozyme gene than does the RNA pol II promoter. Moreover, detection of the AR mRNA by ribonuclease protection assay and of the AR protein level by immunohistochemistry in cultured cells provide direct proof for the hammerhead ribozyme effect in vivo.

EXAMPLE 10

Human Ribozyme Construct for Use in Treatment of Prostate Hyperplasia

The present example defines a method to be used in the treatment of human prostate hyperplasia. The ribozyme construct will include a ribozyme gene sequence as provided in SEQ ID NO: 9 and a promoter sequence from prostate specific antigen gene (PSA). This promoter sequence may be derived from the PSA available at Gen Bank Accession No: U37672.

As part of the claimed invention the method for treating prostate hyperplasia comprises administering a pharmacologically active preparation that includes a vector construct of the ribozyme gene as defined at SEQ ID NO: 9 and a promoter sequence of PSA in an amount effective to reduce antigen receptor gene expression. A pharmacologically active amount of the preparation as used in the description of the present invention as defined as an amount that will provide a reduction of androgen receptor gene expression sufficient to provide a clinically detectable reduction or at least inhibition of prostate gland enlargement.

While any variety of carrier vectors may be employed, it is anticipated that adenoviral and retroviral vector constructs may be used in particular applications of the claimed method. The gene therapy methods provided herein may be used alone or in combination with other treatments, such as surgical removal/reduction of prostate gland and/or administration of enzyme inhibitors, such as alpha reductase. Cyproterone acetate (Schering AG) along with PROSCAR™ (MERCK) may also be employed in combination with the claimed methods to provide improved clinical outcome for the patient.

All of the compositions and methods disclosed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined herein.

The above is a detailed description of particular embodiments of the invention. Those with skill in the art should, in light of the present disclosure, appreciate that obvious modifications of the embodiments disclosed herein can be made without departing from the spirit and scope of the invention. All of the embodiments disclosed and claimed herein can be made and executed without undue experimentation in light of the present disclosure. The full scope of the invention is set out in the claims that follow and their equivalents. The claims and specification should not be construed to unduly narrow the full scope of protection to which the present invention is entitled.

REFERENCES

The following references, to the extent they provide exemplary procedural or other details supplementary to those set forth herein, are specifically incorporated herein by reference.

Adler, A J., Scheller, A, and Robins, D. M. (1993). The stringency and magnitude of androgen-specific gene activation are combinational functions of receptor and nonreceptor binding site sequences. Mol. Cell Biol. 13:6326–35

Adler, A. J., Danielson, M., and Robins, D. M. (1992). Androgen-specific gene activation via a consensus glucocorticoid response element is determined by interaction with nonreceptor factors. Proc. Natl. Acad. Sci. USA 89:11660–3

Adler, A J., Scheller, A, Hoffman, Y., and Robin, D. M. (1991). Multiple components of a complex androgen-dependent enhancer. Mol. Endocrinol. 5:1587–1596

Altman, S. (1989). Ribonuclease P: an enzyme with a catalytic RNA subunit. Adv. Enzymol. 62:1–36

Ammenola, R., Mesuraca, M., Russo, T., and Cimino, F (1992). Spl DNA binding efficiency is highly reduced in nuclear extracts from aged rat tissue. J Biol. Chem. 267:17944–8

Arriza, J. L., Weinberger, L., Cerelli, G., Glaser, T. M., Handelin, B. L., Houseman, D. E., and Evans, R. M. (1987). Cloning of human mineral corticoid receptor complementary DNA. structural and functional kinship with the glucocorticoid receptor. Science 237:268–75

Azizkihan, J. C., Jensen, D. E., Pierce, A. J., and Wade, M. (1993). Transcription from TATA-less promoters: dihydrofolate reductase as a model. Crit. Rev. Euk. Gene Exp. 3:229–54

Baarends, W. M., Themmen, A. P., Blok, L. J., Mackenbach, P., Brinkmann, A. O., Meijer, D., Faber, P. W., Trapman, J., and Grootegoed, J., k (1990). The rat androgen receptor gene promoter. Mol. Cell. Endocrinol. 74 (1):75–84

Barrack, E. R., Bujnovszky, D., and Walsh, P. C. (1983). -Subcellular distribution of androgen receptor in human benign hyperplastic and malignant prostatic tissues: characterization of nuclear salt-resistant receptor. Cancer Res. 43:1107–16

Beato, M. (1989). Gene regulation by steroid hormone. Cell 56:335–44

Belis, J. A. (1980). Methodological basis for the radioimmuniassay of endogenous steroids in human prostic tissue in human. Invest. Urol. 17:332–6

Berg, J. M. (I990). Zinc fingers and other metal-binding domains. J. Biol. Chem. 265:6513–6

Bertrand, E., Pictet, R., and Grange, T. (1994). Can hammerhead ribozymes be efficient tools to inactivate gene function? Nucl. Acids Res. 22 (3):293–300

Bingham, P. M., Scott, M. O., Wang, S., Mcphaul, M. J., Wilson, E. M., Garbem, J. Y., Merry, D. E., and Fischbeck, K H. (1995). Stability of an expanded trinucleotide repeat in the androgen receptor gene in transgenic mice. Nature Genet. 9:191–6

Boles, T. C., and Hogan, M. E. (1987). DNA structure equilibria in the human c-myc gene. Biochemistry 26:367–76

Bolton, N. J., Lukkarine, O., and Vikho, R. (1986). Concentration of androgens in human benign prostate hypertrophic tissues incubated for up to three days. Prostate 9:159–67

Bradford, M. M. (1976). A rapid and sensitive method for the quantitation of microgram quantities of protein utilizing the principle of protein-dye binding. Nucl. Acids Res. 11:1475–89

Bratty, J., Chartrand, P., Ferbeyre, G., and Cedergron, R. (1993). The hammerhead RNA domain, a model ribozyme. Biochim. Biophys. Acta 1216(3):345–59

Brikmann, A. O., Klaasen, P., Kuiper, G. G. J. M., van der Korput, G. M., Bolt, J., deboer, W., Smit, k, Faber, P. W., van Rooij, H. C. J., Geurts-van Kassel, A., Voorhorst, M. M., Mulder, E., and Trapman, T. (1989). Structure and function of the androgen receptor. Urol. Res.17:87–93

Brolin, J., Skoog, G., and Ekman, P. (1992). Immunohistochemistry and biochemistry in detection of androgen, progesterone, and estrogen receptors in benign and malignant human prostatic tissue. Prostate 20:281–95

Brown, T. R., Lubahn, P. B., Joseph, D. R., French, F. S., and Wollard, H. F. (1989). Androgen receptor locus on the human X chromosome: regional localization Xq 11–12 and description of a DNA polymorphism. Am. J. Hum. Genet. 44:264–9

Bruchovsky, N., and Wilson, J. D. (1968). The conversion of testosterone to 5-alpha-androge-17-beta-ol-3-one by rat prostate in vivo and in vitro. J. Biol. Chem. 243(8):2012–21

Buzayan, J. M., Gerlach, W. L., and Bruening, G.(1986). Non-enzymatic cleavage and ligation of RNAs complementary to a plant virus satellite RNA. Nature 323:349–53

Cameron, F. H., and Jennings, P. A. (1989). Specific gene suppression by engineered ribozymes in monkey cells. Proc. Natl. Aced. Sci. USA 86:9139–43

Cech, T. R. (1989). Self-splicing and enzymatic activity of an intervening sequence RNA from Tetrahymena. A New Chem. Int. ed. Engi. 29:759–68

Chakravarti, D., Lamate, V. J., Nelson, M. C., Nakajiima, J., Schulman, [. G., Jugullon, M., Montiminy, M., and Evans, M. (1996). Role of CBP/p3OO in nuclear receptor. Nature, in press Chan, J., Song, C. S., Chaftedee, B., and Roy, A. K (1995). Enzymatic inactivation of androgen receptor function by dehydroepiandrosterone sulfotransferase in a human prostatic adenocarcinoma cell line transfected with expression vector. 77th Endocrine Society Meeting 77:503

Chang, C., Saltzman, A, Yeh, S., Young, W., Keller, E., Lee, H. J., Wang, C., and Mizokami, A (1995). Androgen receptor an overview. Crit. Rev Eukar. Gene Exp. 5:97–125

Chang, C. S., Kokontis, J., and Liao, S. T. (1988a). Molecular cloning of human and rat complementary DNA encoding androgen receptors. Science 240:324–6

Chang, C. S., Kokontis, J., and Liao, S. T. (1988b). Structural analysis of complementary DNA and amino acid sequences of human and rat androgen receptors. Proc. Natl. Acad. Sci. USA 85(19):7211–5

Chang, C., Whelen, C., Popovich, T., Kokontin, J. and Liao, S. (1989). Fusion proteins containing androgen receptor sequences and their use in the production of poly and monoclonal anti-androgen receptorantibodies. Endocrinology 125:1097–9

Chatterjee, B., Song, C. S., Jung, M. H., Chen, S., Walter, C. A., Herbert, D. C., Weaker, F. J., Mancini, M. A., and Roy, A. K (1996). Targeted overexpression of androgen receptor with a liver-specific promoter in transgenic mice. Proc. Natl. Acad. Sci. USA 93(2):728–33

Chen, C. J'., Banedea, A. C., Haglund, K, Harmison, G. G., and Schubert, M. (1992). Inhibition of HIV-1 replication by novel multitarget ribozymes. Ann. New York Acad. Sci. 660:271–3

Cho, H., and Katzenellenbogen, B. S. (1993). Synergistic activation of estrogen receptor-mediated transcription by estradiol and protein kinase activators. Mol. Endocrinol. 7(3):441–52

Choong, C. S., Kemppainen, J. k, Zhou, Z. X., and Wilson, E. M. (1996). Reduced androgen receptor gene expression with first exon CAG repeat expansion. Mol. Endocrinol. 10:1527–35

Chowrira, B. M., Pavco, P. k, and McSwiggen, J. K. (1994). In vitro and in vivo comparison of hammerhead, hairpin, and hepatitis delta virus self-processing ribozyme cassettes. J. Biol. Chem. 269 (41):25856–64

Christoffersen, R. E., and Marr, J. J. (1995). Ribozyme as human therapeutic agents. J. Med. Chem. 38:2023–37

Coffey, D. S. (1988). Androgen action in the sex accessary tissues. in: Knobil J. and Neil, J., eds. The Physiology of Reproduction. pp 1081–119

Cohen, J. S., and Hogan, M. E. (1994). The new genetic medicines. Sci. Am. 271(6):76–82

Cooney, M., Czermuszewicz, G., Postel, E. M., Flint, S. J., and Hogan, M. E. (1988). Site-specific oligonucliotide binding represses transcription of the human c-myc gene in vitro. Science 241:456–9

Cotten, M. (1990). The in vivo application of ribozymes. Trends Biotechnol. 8(7):174–8

Cotten, M., and Birnstiel, M. (1989). Ribozyme mediated destruction of RNA in vivo. EMBO J. 8(12):3861–6

Culig, Z., Hobisch, A., Cronaner, M. V., Cato, kC. B., Hiftmair, A., Rad-mayr, C., Ederie, J., Bartsch, G., and Klocker, H. (1993). Mutant androgen receptor detected in an advanced-stage prostatic carcinoma is activated by adrenal androgens and progesterone. Mol. Endocrinol. 7:1541–50

Dai, L. J., and Bumstein, K L. (1996). Two androgen response elements in the androgen receptor coding region are required for cell-specific up-regulation of receptor messager RNA Mol. Endocrinol. 10: 1 582–94

Das, G., Henning, D., and Reddy, R. (1988). Upstream regulatory elements are necessary and sufficient for transcription of a U6 RNA gene by RNA polymerase Ill. EMBO J. 7:503–12

De Vos, P., Claessens, F., Peelers, B., Rombauts, W., Heyns, W., and Verhoeven, G. (1993). Interaction of androgen and glucocorticoid receptor DNA binding domains with their response elements. Mol. Cell. Endocrinol. 90(2):R1 16

De Vos, P., Claessens, F., Winderickx, J., Van Dijck, P., Celis, L., Peeters, B., Rombauts, W., Heyns, W., and Verhoeven, G. (1991). Interaction of androgen response elements with the DNA-binding domain of the rat androgen receptor expressed in *Escheiichia coli*. J. Biol. Chem. 266(6):3439–43

Denner, L..k, Weigel, N. L., Maxwell, B. L., Schrader, W. T., and O'Malley, B. W. (1990). virusoid and a structural model for the active sites. Cell 49(2):211–20

Fox, K R. (1994). Formation of DNA triple helices in corporation blocks of G:GC and T:AT triplets using short acridine-linked oligonucleotide. Nucl. Acids Res. 22:2016–21

Frank-Kamenetskii, M. D., and Mirkin, S. M. (1995). Triplex DNA structures. Annu. Rev. Biochem. 64:65–95

Genersch, E., Eckerskorn, C., Lottespeich, F., Herzog, C., Kuhn, K, and Poschl, E. (1995). Purification of the sequence specific transcription factor CTCBF involved in the control of human collagen IV genes, subunits with homology to Ku antigen. EMBO J. 14:791–800

Garber, H., Seipel, K, Georgiev, O., Hofferer, M., Hug, M., Rusconi, S., and. Schaffner W. (1994). Transcriptional activation modulated by homopolymeric glutamine and proline stretches. Science 263:808–11

Gesteland, R. F., and Alkins, J. F. (1993). The RNA world, monograph 24, Cold Spring harbor Laboratory Press, Plainview, N.Y.

Goodchild, J., and Kohli, V. (1991). Ribozyme that cleaves an RNA sequence for human immunodeficiency virus: the effect of flanking sequence on rat. Arch. Biochem. Biophys. 284:386–91

Goueli, S. A, Holtzman, J. L., and Ahmed, K (1984). Phosphorylation of the androgen receptor by a nuclear cAMP-independent protein kinase. Biochem. Biophys. Res. Commun. 123(2):778–84

Greenberg, N. M., DeMayo, F. J., Sheppard, P. C., Barrios, R., Lebovitz, R., Finegoid, M., Angelopoulou, R., Dodd, J. G., Duckworth, M. L., Rosen, J. M., and Matusik, R. J. (1994). The rat probasin gene promoter direct hormonally regulated expression of a heterologous gene specifically to the prostate in transgenic mice. Mol. Endocrinol. 8:230–9

Griffin, J. E., and Wilson, J. D. (1989). The androgen resistance syndrome, 5-reductase deficiency, testicular terminization and related disorders, In the metabolic basis of inherited disease. Scriver, C. R., Beaude, A. L., Sly, W. S., and Walle, O., eds., pp 1919–44, Mcgraw-Hill, New York Grigoriew, M., Praseath, P., Robin, P., and Hemer, A (1992). A triple helixforming oligonucleotide-intercalater conjugate acts as a transcriptional repression inhibition of NF-I<B binding to interleukin-2 receptor a regulatory sequence. J. Biol. Chem. 267:3389–3395

Grossman, M., Lindzey, J., Kumar, M. V., and Tinall, D. L. (1994). The mouse androgen receptor is suppressed by the 5'-untranslated region of the gene. Mol. Endocrinol. 8:448–55

Grossmann, M. E., and Tindall, D. J. (1995). The androgen receptor is transcriptionally suppressed by proteins that bind single-stranded DNA. J. Biol. Chem. 270 (18):10968–75

Grumback, M. M., and Conte, F. A. (1992). Disorders of sex differentiation. In Textbook of Endrocrinology. J. D. Wilson and D. W. Foster, eds, 8th ed., pp 853951. Harcourt Brace J. Vanovich, Philadelphia Guerrier-Takada, C., Gardiner, K, Marsh, T., Pace, N., and Altman, S. (1983). The RNA moiety of ribonuclease P is the catalytic subunit of the enzyme. Cell 35:849–57

Gumucio, D. L., Shelton, D. A, Bailey, W. J., Slightom, J. L., and Goodman, M. (1993). Phylogenetic footprinting reveals unexpected complexity in trans factor binding upstream from the epsilon-globin gene. Proc. Nati. Acad. Sci. USA 90:6018–6022

Ha, J., and I<jm, K H. (1994). Inhibition of fatty acid synthesis by expression of an acetyl-CoA carboxylase-specific ribozyme gene. Proc. Natl. Acad. Sci. USA 91(21):9951–5

Hagon, G., Denning, J., Preib, k, Beato, M., and Suske, G. (1995). Functional analyses of the transcription factor Sp4 reveal properties distinct from Sp1 and Sp3. J. Biol. Chem. 270:24989–94

Hampel, A, and Tritz, R. (1989). RNA catalytic properties of the minimum (–) s TRSV sequence. Biochemistry 28 (12):4929–33

Hanseein, B., Eckner, R., Direnzo, J., Halchhmi, S., Liu, H., Seary, B., and Brown, M. (1996). p3OO is a component of an estrogen receptor coactivator complex. Proc. Natl. Acad. Sci. USA, in press Haseloff, J., and Gerlach, W. L. (1989). Sequences required for self-catalysed cleavage of the satellite RNA of tobacco ringspot virus. Gene 82 (1):43–52

Haseloff, J., and Gerlach, W. L. (1988). Simple RNA enzymes with new and highly specific endoribonuclease activities. Nature 334:585–91

Hattori, M', Tugores, A., Veloz, L., Karin, M., and Brenner, D. A (1990). A simplified method for the preparation of transcriptionally active liver nuclear extracts. DNA Cell Biol. 9:777–81

He, W. W., Fischer, L. M., Sun, S., Bilhartz, D. L., Zhu, X. P., Young, C. Y., Kelley, D. B., and Tindall, D. J. (1990). Molecular cloning of androgen receptors from divergent species with a polymerase chain reaction technique: complete CDNA sequence of the mouse androgen receptor and isolation of androgen receptor CDNA probes from dog, guinea pig and clawed frog. Biochem. Biophys. Res. Commun. 171(2):697–704

Heidenreich, V., and Eckstein, F. (1992). Hammerlead ribozyme-mediated cleavage of the long terminal repeat RNA of Human Immunodeficiency virus type 1. J. Biol. Chem. 267:1904–9

Helpap, B. (1992). Pathology of benign prostatic hyperplasia. In Benign prostatic disease. W. Vahlensieck and G. Rulishauser, eds., Georg Thieme Verlag, New York, pp 84–97

Hendrix, C., Anne, J., Joris, B., Van-Aerschot, A., and Herdewijn, P. (1996). Selection of hammerhead ribozymes for optimum cleavage of interieukin 6 mRNA. Biochem. J. 314:655–61

Herschlag, D. (1991). Implications of ribozyme kinetics for targeting the cleavage of specific RNA molecules in vivo: more isn't always better. Proc. Natl. Acad. Sci. USA 88(16):6921–5

Herschlag, D., and Cech, T. R. (1990). Catalysis of RNA cleavage by the *Tetrahymena thermophila* ribozyme. Knetic description of the reaction of an RNA substrate complementary to the active site. Biochemistry 29(44): 10159–71

Hirst, J. J., West, N. B., Brenner, R. M., and Novy, M. J. (1992). Steroid hormone receptors in the adrenal glands of fetal and adult rhesus monkeys. J. Clin. Endocrinol. Metab. 75(i):308–14

Ho, S. P., and Britton, D. H. (1992). Catalytic RNA molecules and their cleavage of viral mRNA. Ann. New York Aced. Sci. 660:265–7

Hoffaman, E. K, Trusko, S. P., Murphy, M., and George, D. (1990). An SI nuclease-sensitive homopurine-homopyrimidine domain in the c-ki-ras promoter interacts with a nuclear factor. Proc. Natl. Acad. Sci. USA 87:2705–9

Holienberg, S. M., Weinberger, C., Ong, E. S., Cerelli, G., Oro, k, Lebo, R., Thompson, E. B., Rosenfeld, M. G., and Evans, R. M. (1985). Primary structure and expression of a functional human glucocorticoid receptor cDNA. Nature 318:635–41

Hollingsworth, M., Closken, C., Harris, k, McDonald, C. D., Pahwa, G. S., and Maher, L. J. III (1994). A nuclear factor that binds purine-rich, single-stranded oligonucleotides derived from SI-sensitive elements upstream of the CFTR gene and MUC1 gene. Nucl. Acids Res. 22:1138–46

Homann, M., Tzortzakaki, S., Riftner, K, Sczakiel, G, and Tabler, M. (1993). Incorporation of the catalytic domain of a hammerhead ribozyme into antisense RNA enhances its inhibitory effect on the replication of human immunodeficiency virus type 1. Nucl. Acids Res. 21(12):2809–14

Hong, H., Kohli, K, Trivedi, A., Johnson, D. L., and Stallcup, M. R. (1996). GRIPI, a novel mouse protein that serves as a transcriptional coactivator in yeast for the hormone binding domains of steroid receptors. Proc. Nati. Acad. Sci. USA 93(10):4948–52

Horie, K, Takakura, K, Fujiwara, H., Suginami, H., Liao, S., and Mori T. (1992). Immunohistochemical localization of androgen receptor in the human ovary throughout the menstrual cycle in relation to oestrogen and progesterone receptor expression. Hum. Reprod. 7(2):184–90

Horwitz, K B., Jackson, T., K, Bain, D. L., Richer, J. K, Takimoto, G. S., and Tung, L. (1996). Nuclear receptor coactivator and corepressor. Mol. Endocrinol. 10:1167–77

Hutchison, K k, Dittmar, K D., and Pratt, W. B. (1994). All of the factors required for assembly of the glucocorticoid receptor into a functional heterocomplex with heat shock protein 90 are preassociated in a self-sufficient protein folding structure, a "foldosome" J. Biol. Chem. 269(45): 27894–9

Imasaki, K, Okab, T., Mupakami, H., Tauaka, Y., Huji, M., Takayanagi, R., and Nawata, H. (1996). Androgen insensitivity syndrome due to new mutations in the DNA-binding domain of the androgen receptor. Mol. Cell. Endocrinol. 120:15–24

Ing, N. H., Beekman, J. M., Kessler, D. J., Murphy, M., Jayaraman, K, Zendergui, O. G., Hogan, M. E., O'Malley, B. W., and Tsai, M. J. (1993). In vitro transcription of a progestrone-responsive gene is specifically inhibited by a triplex-forming oligonucleotide. Nucl. Acids Res. 21:2789–96

Inokuchi, Y., Yuyama, N., Hirashima, A-, Nishikawa, S. AU., Ohkawa, J., and Taira, K (1994). A hammerhead ribozyme inhibits the proliferation of an RNA coliphage SP in *Escherichia coli*. J. Biol. Chem. 269(15):11361–6

Isaacs, J. T., and Coffey, D. S. (1989). Etiology and disease process of benign prostatic hyperplasia. Prostate 2:33–50

Isaacs, J. T., and Kyprianou, N. (1987. Development of androgen-independent tumor cells and their implication for the treatment of prostatic cancer. Urol. Res. 15(3): 133–8

Janne, O. A., and Shan, L. X. 1991). Structure and function of the androgen receptor. Ann. N Y Acad. Sci. 626:81–91

Jarvis, T. C., Wincott, F. E., Alby, L. T., McSiviggen, J. A., Beigelman, L.,. Gustofson, J., DiRenzo, A., Levy, K, Arthour, M., Matulic-Adamic, J., Karpeisky, A., Gonzalez, C., Woolf, T. M., Usman, N., and Stinchcomb, D. T. (1996). Optimizing the cell efficiency of synthetic ribozyme. J. Biol. Chem. 268:24515–8

Jenster, G., Trapman, J., and Brinkmann, A. O. (1993). Nuclear import of the human androgen receptor. Biochem. J. 293(3):761–8

Jenster, G., van der Korput, H. A., van Vroonhoven, C., van der Kwast, T. H., Trapman, J., and Brinkmann, A. O. (1991). Domains of the human androgen receptor involved in steroid binding, transcriptional activation, and subcellular localization. Mol. Endocrinol. 5(10) :1396–404

Johson, A, Jinno, Y., and Merlino, G. T. (1988). Modulation of epidermal growth factor receptor proto-oncogene transcription by a promoter site sensitive to SI nuclease. Mol. Cell. Biol. 8:4174–84

Joseph, S., and Burke, J. M. (1993). Optimization of an anti-HIV hairpin ribozyme by in vitro selection. J. Biol. Chem. 268(33):24515–8

Kaku, A., Chang, C., Okamoto, T., Tamura, T., and Yoshimura, T. (1993). Immunolocalization of androgen receptor in the clonal gland of male. Jpn.Poultry. Sci. 30:413–8

Kallioniemi, P., and Visakorpi, T. (1996). Genetic basis and clonal evolution of human prostate cancer. Adv. Cancer Res. 68:225–55

Kalloo, N. B., Gearhart, J. P., and Barrack, E. R. (1993). Sexually dimorphic expression of estrogen receptors, but not of androgen receptors in human fetal external genitalia. J. Clin. Endocrinol. Metab. 77(3):692–8

Kamei, Y., Xu, L., Heinzel, T., Torchia, J., Kurokawa, R., Gloss, B., Lin, S. C., Heyman, R. A,, Rose, D. W., Glass, C. K, and Rosenfeld, M. G. (1996). A CBP integrator complex mediates transcriptional activation and AP-1 inhibition by nuclear receptors. Cell 85(3):403–14

Kashani-Sabet, M., Funato-Tone, T., Jiao, L., Wang, W., Yoshida, E., Kashfinn, B. I., Shitara, T., Wu, A. M., and Moreno, J. G. (1992). Reversal of the malignant phenotype by an anti-ras ribozyme. Antisense Res.Dev. 2(1): 3–15

Kemppainen, J. A., Lane, M. V., Sar, M., and Wilson, E. M. (1992). Androgen receptor phosphorylation, turnover, nuclear transport, and transcriptional activation: specificity for steroids and antihormones. J. Biol. Chem. 267(2):968–74

Kobayashi, H., Dorai, T., Holland, J. F., and Ohnuman, T. (1994). Reversal of drug sensitivity of multidrug-resistant tumor cells by an MDR1 (RGYI) ribozyme. Cancer Res. 54:1271–5

Kuiper, G. G., de Ruiter, P. E., and Brinkmeinn, A. O. (1992). Androgen receptor heterogeneity in LNCaPcells is caused by a hormone independent phosphorylation step. J. Steroid Biochem. Mol. Biol. 41(3–8):697–700

Kuiper, G. G., De Ruiter, P. E., and Brinkmann, A. O. (1993). Androgen receptor phosphorylation. Ann. New York Acad. Sci. 684:224–6

Kumar, K V., Jones, E. A., Grossmann, M. E., Blexrud, M. D., and Tindall., D. J. (1994). Identification and characterization of a suppressor element in the 5'-flanking region of the mouse androgen receptor gene. Nucl. AC71d Res. 22:3693–3698

Kwok, R. P., Lundblad, J. R., Chrivia, J. C., Richards, J. P., Bachinger, H. P., Brennan, R. G., Roberts, S. G., Green, M. R., and Goodman, R. H. (1994). Nuclear protein CBP is a coactivator for the transcription factor CREB. Nature 370:223–6

L'Huilillier, P. L., Davis, S. R., and Bellamy, A. R. (1992). Cytoplasmic delivery of ribozyme in a-lactalumin mRNA levels in C127 mouse cell. EMBO J. 11:4411–8

L'Huillier, P. J., Soulier, S., Stinnakre, M. G., Lepourry, L., Davis, S. R., Mercier, J. C., and Vilofte, J. L. (1996). Efficient and specific ribozyme-mediated reduction of bovine aplpha-lactoalbumin expression in double transgenic mice. Proc. Natl. Acad. Sci. USA 93:6698–703

La Spada, k R., Wilson, E. M., Lubahn, D. B., Harding, A. E., and Fischbeck, K H. (1991). Androgen receptor gene mutations in X-linked spinal and bulbar muscularatrophy. Nature 352:77–9

La Spada, A. R., Roling, D. B., Harding, A. E., Warner, C. L., Spiegel, R., Hausmanowa-Petrusewicz, 1., Yee, W. C., and Fischbeck, K H. (1992). Meiotic stability and genotype-phenotype correlation of the trinucleotide repeat in X-linked spinal and bulbar muscular atrophy. Nature Genet. 2(4):301–4

Lafyatis, R., Denhez, F., Willians, T., Spom, N., and Roberts, A (1991). Sequence specific protein binding to and activation of the TGFx3 promoter through a repeated TCCC motif. Nucl. Acids Res. 23:6419–25

Lange, W., Cantin, E. M., Finke, J., and Dolken G. (1993). In vitro and in vivo effects of synthetic ribozymes targeted against BCR/ABL MRNA. Leukemia 7(11):1786–94

Larsson, S., Hotchkiss, G., Andang, M., Nyholm, T., Inzunza, J., Jansson, I., and Ahrlund-Richter, L. (1994). Reduced beta 2-microglobulin mRNA levels in transgenic mice expressing a designed hammerhead ribozyme. Nucl. Acids Res. 22(12):2242–8

Lepor, H., and Lawson, P. (1993). Prostate cancer. W. B. Saunders Company. Philadelphia-London-Toronto-Montreal-Sydney-Tokyo Lieber, A., and Stranss, M. (1996). Selection of efficient cleavage sites in target RNAs by using a ribazyme expression library. Mol. Cell Biol. 15:540–51

Lindzey, J., Grossmann, M., Kumar, M. V., and Tindall, D. J. (1993). Regulation of the 5'-flanking region of the mouse androgen receptor gene by CAMP and androgen. Mol. Endocrinol. 7(12):1530–40

Lindzey, J., Kumar, M. V., Grossman, M., Young, C., and Tindall, D. J. (1994). Molecular mechanisms of androgen action. Vitam. Horm. 49:383–432

Long, D. M., and Uhlenbeck, O. C. (1993). Self-cleaving catalytic RNA FASEB 7(1):25–30 Lubahn, D. B., Joseph, D. R., Sullivan, P. M., Willard, H. F., French, F. S., and Wilson, E. M. (1988). Cloning of human androgen receptor complementary DNA and localization to the X chromosome. Science 240:327–30

Lyamichev, V. I., Mirkin, S. M., and Frank-Kamenetskii, M. D. (1986). Structures of homopurine-homopyrimidine tract in superhelical DNk J. Biomol. Struct. Dyn. 3:667–9

Macke, J. P., Hu, N., Hu, S., Bailey, M. U., King, V. L., Brown, T., Hamer, D., and Nathans, J. (1993). Sequence variation in the androgen receptor gene is not a common determinant of male sexual orientation. Am. J. Hum. Genet. 53(4):84452

MacLean, H. E., Chu, S., Wame, G. L., and Zajac, J. D. (1993). Related individuals with different androgen receptor gene deletions. J. Clin. Invest. 91(3):1123–8

MacLean, H. E., Cho, W. T., Rekaris, G., Wame, G. L., and Zajac, J. D. (1995). Abnormal androgen receptor binding affinity in subjects with Kennedy's disease (spinal and bulbar muscular atrophy). J. Clin. Endocrinol. Metab. 80(2):508–16

Mangelsdorf, D. J., Thummel, C., Beato, M., Herrlich, P., Schutz, G., Umesono, K, Blumberg, B., Kastner, P., Mark, M., and Chambon, P. (1995). The nuclear receptor superfamily: the second decade. Cell 83:835–9

Mayfield, C., Ebbinghaus, S., Gee, J., Jones, D., Rodu, B., Squibb, M. A. U., and Miller, D. (1994). Triplex formation by the human Ha-ras promoter inhibits Spl binding and in vitro transcription. J. Biol. Chem. 269(27): 18232–8

McGinnis, M. Y., and Yu, W. H. (1995). Age-related changes in androgen receptor levels in cranial nerve nuclei of male rats. Brain Res. Bull. 36(6):581–5

Mhatre, k N., Trifiro, M.,k, Kaufman, M., Kazemi-Esfadani, P., Figiewicz, D., Rouleau, G., and Pinsky, L. (1993). Reduced transcriptional regulatory competence of the androgen receptor in X-linked spinal and bulbar muscular atrophy. Nature Genet. 5(2):184–8

Michienzi, k, Prislei, S., and Bozzoni, 1. (1996). U1 small nuclear RNA chimeric ribozymes with substrate specificity for the Rev pre-mRNA of human immunodeficiency virus. Proc. Natl. Acad. Sci. USA 93(14):7219–24

Migeon, C. J., Berkovitz, G. O., and Brown, T. R. (1994). Sexual differentiation and ambiguity. In Kappy, M. S., Blizzard, R. M., Migeon, C. J., eds, The diagnosis and treatment of endocrine disorder in childhood and adolescence. Springfield, Ill.: Charles C Thomas. pp 573–715

Misrahi, M., Atger, M., d'Auriol, L., Loosfelt, H., Meriel, C., Fridlansky, F., Guiochon-Mantel, A., Galibert, F., and Milgrom, E. (1987). Complete amino acid sequence of the human progesterone receptor deduced from cloned cDNA. Biochem. Biophys. Res. Commun. 143(2):740–8

Mizokami, k, and Chang, C. (1994). Induction of translation by the 5'-untransiated region of human androgen receptor MRNA. J. Biol. Chem. 269:25655–25659

Mizokami, A., Yeh, S. Y., and Chang, C. (1994). Identification of 3', 5'-cyclic adenosine monophosphate response element and other cis-acting elements in the human androgen receptor gene promoter. Mol. Endocrinol. 8(1): 77–88

Moudgil, V. K (1990). Phosphorylation of steroid hormone receptors. Biochim. Biophys. Acta 1055(3):243–58

Mouscadet, J. F., Carteau, S., Goulaouic, H., Subra, F., and Auclair, C. (1994). Triplex-mediated inhibition of HIV DNA integration in vitro. J. Biol. Chem. 269(34):21635–8

Murtha, P., Tindall, D. J., and Young, C. Y. (1993). Androgen induction of a human prostate-specific kallikrein, hKLK2:characterization of an androgen response element in the 5' promote region of the gene. Biochemistry 32(25): 6459–64

Naldini, et al., (1996). In vivo gene delivey and stable transduction of non-dividing cells by a lentiviral vector. Science 272:263–267

Nensehmid-kaspar, F., Gast, A, Peterziel, H., Schneikert, J., Muigg, A, Ransmayr, G., KJocker, H., Bartsch, G., and Lato, A C. B. (1996). CAG-repeat expansion in androgen receptor in Kennedy's disease is not a loss of function mutation. Mol. Cell. Endocrinol. 117:149–56

Newmark, J. R., Hard, D. O., Tonb, D. C., Carter, B. S., Epstein, J.1., Isaacs, W. B., Brown, T. R., and Barrack, E. R. (1992). Androgen receptor gene mutations in human prostate cancer. Proc. Natl. Acad. Sci. USA 89(14):6319–23

Ohkawa, J., Koguma, T., Kohda, T., and Taira, K (1995). Ribozymes: from mechanistic studies to applications in vivo. J. Biochem. 11 8(2):251–8

Ohta, Y., Kijima, H., Ohkawa, T., Kashani-Sabet, M., and Scanlon, K J. (1996). Tissue-specific expression of an anti-ras ribozyme inhibits proliferation of human malignant melanoma cells. Nucl. Acids Res. 24:938–42

Ojwang, J. O., Hempel, A., Looney, D, J., Wong-Staal, F., and Rappaport, J. (1992). Inhibition of human immunodeficiency virus type 1 expression by a hairpin ribozyme. Proc. Nat'l. Acad. Sci. USA 89(22):10802–6

Onate, S. A., Tsai, S. Y., Tsai, M. J., and O'Malley, B. W. (1995). Sequence and characterization of a coactivator for the steroid hormone receptor superfamily. Science 270:1354–7

Perreault, J. P., Labuda, D., Usman, N., Yang, J. H., and Cedergren, R. (1991). Relationship between 2'-hydroxyls and magnesium binding in the hammerhead RNA domain: a model for ribozyme catalysis. Biochemistry 30(16):4020–5

Perriman, R., Bruening, G., Bennis, E. S., and Peacock, W. J (1996). Effective ribozyme delivery in plant cells. Proc. Natl. Acad. Sci. USA 93:7219–24

Picard, D., and Yamamoto, K R. (1987). Two signals mediate hormonedependent nuclear localization of the glucocorticoid receptor. EMBO J. 6(11):3333–40

Plavec, J., Thibaudeau, C., and Chaftopadhyaya, J. (1994). How does the 2'-hydroxy group drive the pseudorotational equilibrium in nucleoside and nucleotide by the tuning of 3'-gauche effect. J. Am. Chem. Soc. 116:6558–60

Pratt, W. B. (1990). Interaction of hsp9O with steroid receptors: organizing some diverse observations and presenting the newest concepts. Mol. Cell. Endocrinol. 74(1):69–76

Prins, G. L., Jung, M. H., Vellanoweth, R. L., Chafterjee, B., and Roy, A. R. (1996). Age-dependent expression of the androgen receptor gene in the prostate and its implication in glandular differentiation and hyperplasia. Dev. Genet. 18:99–1

Prody, G. A, Bakos, J. T., Buzayan, J. M., Schaeider, I. R., and Braening, G. (1986). Autolytic processing of dimeric plant virus satelite DNA. Science 231:1577–80

Pugh, B. F., and Tjian, R. (1991). Transcription from TATA-less promoter requires a multisubunit TFIID complex. Genes Dev. 5:1935–45

Pyle, A. M. (1993). Ribozymes: a distinct class of metalloenzymes. Science 261:709–14

Quarmby, V. E., Yarbrough, W. G., Lubahn, D. B., French, F. S., and Wilson, E. M. (1990). Autologous down-regulation of androgen receptor messenger ribonucleic acid. Mol. Endocrinol. 4(1):22–8

Quigley, C., A, De Bellis, A., Marschke, K B., el-Awady, M. K, Wilson, E. M., and French, F. S. (1995). Androgen receptor defects: historial, clinical and molecular perspectives. Endocr. Rev. 16:271–89

Radanyi, C., Chambraud, B., and Baulieu, E. E. (1994). The ability of the immunophilin FKBP59-HBI to interact with the 90-kDa heat schock protein is encoded by its tetratri copeptides repeat domain. Proc. Nat'l. Acad. Sci. USA 91:11197–201

Ris-Stalpers, C., Verleun-Mooijman, M. C., Trapman, J., Brinkmann, A. O., Threonine, O. N. (1993). Amino acid position 868 in the human androgen receptor is essential for androgen binding specificity and functional activity. Biochem. Biophys. Res. Commun. 196(1):173–80

Rossi, J. J., and Sarver, N. (1990). RNA enzymes (ribozymes) as antiviral therapeutic agents. Trends Biotechnol. 8(7):179–83

Roy, C. (1993). Inhibition of gene transcription by purine rich triplex forming oligodeoxyribonucleotides. Nucl. Acids Res. 21(12):2845–52

Roy, A. K, and Chaftedee, B. (1995). Androgen action. Cri. Rev. Eukary. Gene Exp. 5 (2):157–76

Ruffner, D, E., Stormo, G. D., and Uhlenbeck, O. C. (1990). Sequence requirements of the hammerhead RNA self-deavage reaction. Biochemistry 29(47):10695–702

Ruizeveld-de-Winter, J. A., Trapman, J., Vermey, M., Zegers, N. D., van der, Kwast Th. (1991). Androgen receptor expression in human tissues. an immunohistochemical study. J. Histochem. Cytochem. 39(7):927–36

Rundiett, 'S. E., Wu, X. P., and Miesfeld, R. L. (1990). Functional characterizations of the androgen receptor confirm that the molecular basis of androgen action is transcriptional regulation. Mol. Endocrinol. 4(5):708–14

Sai, T., Seine, S., Chong, C., Trifiro, M., Prinsky, L., Mhatre, A., Kautman, M., Lambert, B., Trapman, J., Brinkmann, A. O., Rosenfield, R. L., and Liao, S. (1990). An exonic point mutation of the androgen receptor gene in a family Vith complete androgen insensitivity. Am. J. Hum. Genet. 46:1095–100

Sanfacon, H. and Hohn, T. (1990). Proximity to the promoter inhibits recognition of cauliflower mosaic virus polyadenylation signal. Nature 346:81–4

Bar, M., Lubahn, D. B., French, F. S., and Wilson, E. M. (1990). Immunohistochemical localization of the androgen receptor in rat and human tissues. Endocrinology 127:3180–6

Sarver, N., Cantin, E. M., Chang, P. S., Zaia, J. A., Ladne, P..k, Stephens, D. A., and Rossi, J. J. (1990). Ribozymes as potential anti-HIV-1 therapeutic agents. Science 247:1222–5

Sasson-Corsi, P. (1996) Same clock, different work. Nature 384:613–4

Sauman, I., and Reppert, S. M. (i996). Circadian clock neurons in the silkmoth anthreaea pernyi: novel mechanisms of period protein regulation. Neuron 17:889–900

Sauman, I., Tsai, T., Roca, A. L., and Reppert, S. M. (1 196). Period protein is necessary for circadian control of egg hatching behovior in the silkmoth antheraea pemyi. Neuron 17:901–9

Saxena, S. K, and Ackerman, E. J. (1990). Ribozymes correctly cleave a model substrate Ind endogenous RNA in vivo. J. Biol. Chem. 265:17106–17109

Scanlon, H., and Hohn, T. (1990). Proximity to the promoter inhibit recognition of cauliflower mosaic virus polyadenylation signal. Nature 348:81–4

Scanlon, K J., Jiao, L., Funato, T., Wang, W., Tone, T., Rossi, J. J., and Kashani-Sabet, M. (1991). Ribozyme-mediated cleavage of c-fos mRNA reduces gene expression of DNA synthesis enzymes and metallothionein. Proc. Nat'l. Acad. Sci. USA 88(23):10591–5

Schuur, et al., (1996). Prostate-Specific Antigen Expression is Regulated by an Upstream Enhancer. The Journal of Biological Chemistry. 271(12)7043–7051.

Shimayama, T. (1994). Effect of deoxyribonucleotide substitutions in the substrate strand on hammerhead ribozyme-catalyzed reactions. Gene 149:41–6

Shimayama, T., Nishikawa, S., and Taira, K (1995). Generality of the UX rule: kinetic analysis of the results of systematic mutations in trinucleotide at the cleavage site of hammerhead ribozyme. Biochemistry 34:3649: 54

Siiteri, P. K, and Wilson, J. D. (1970). Dihydrotestosterone in prostatic hypertrophy. I. The formation and content of dihydrotestosterone in the hypertroptiic prostate of man. J. Clin. Invest. 49(9): 1737–45

Simental, J. A., Bar, M., Lane, M. V., French, F. S., and Wilson, E. M. (1991). Transcriptional activation and nuclear targeting signals of the human androgen receptor. J. Biol. Chem. 266(1):510–18

Sioud, M., and Drlica, K (1991). Prevention of human immunodeficiency virus type I intergrase expression in Escherichia cofi by a ribozyme. Proc. Nat'l. Acad. Sci. USA 88:7303–7

Sioud, M., Opstad, A., Zhao, J. Q., Levitz, R., Benham, G., and Drlica, K (1994). In vivo decay kinetic parameters of hammerhead ribozyme. Nucl. Acids Res. 22:5571–5, Sioud, M. (1996). Ribozyme modulation of lipopolysaccharide-induced tumor necrosis factor-a production by peritoneal cell in vitro and vivo. Eur J. Immunol. 26:1026–31

Smith, C. L., Conneely, O. M., and O'Malley, B. W. (1993). Modulation of the ligand-independent activation of the human estrogen receptor by hormone and antihormone. Proc. Nat'l. Acad. Sci. USA 90 (13):6120–4

Smith, C. L., Onate, S., Tsai, M. J., and O'Malley, B. W. (1996). CREB binding protein acts synergistically with steroid receptor coactivator-I to enhance steroid receptor-dependent transcription. Proc. Nat'l. Acad. Sci. USA 93:8884–8

Smith, D. F., Faber, L. E., and Toft, D. O. (1990). Purification of unactivated progesterone receptor and identification of novel receptor-associated proteins. J. Biol. Chem. 265(7):3996–4003

Song, C. S., Her, S., Slomczynska, M., Choi, S. J., Jung, M. H., Roy, A. K, and Chafterjee' B. (1993). A distal activation domain is critical in the regulation of the rat androgen receptor gene promoter. Biochem. J. 294(3):779–84

Stefanis, C., Papapetropoulos, T. H., Scarpalezos, S., Lygidakis, G., and Panayiotopoulos, C. P. (1975). X-linked spinal and bulbar muscular atrophy of late onset. A separate type of motor neuron disease? J. Neurol. Sci. 24 (4):493 –503

Steinecke. P., Steger, G., and Schreier, P. H. (1994) A stable hammerhead ribozyme structure is not required for endonucleolytic activity. Gene 149:47–54

Su, W., Jackson, S., Tjian, R., and Echols, H. (1991). DNA looping between sites for transcriptional activation: self-association of DNA-bound Sp1. Genes Dev. 5:820–826

Sullenger, B.,k, and Cech, T. R. (1993). Tethering ribozymes to a retroviral packaging signal for destruction of viral RNA. Science 262:1566–9

Supakar, P. C., Jung, M. H., Song, C. S., Chatterjee, B., and Roy, A. K (1995). Nuclear factor kappa B functions as a negative regulator for the rat androgen receptor gene and NF-kappa B activity increases during the age-dependent desensitization of the liver. J.Biol Chem. 270(2):837–42

Supakar, P. C., Song, C, S., Jung, M. H., Slomczynska, M. A, Kim, J. M., Vellanoweth, R. L., Chatterjee, B., and Roy, A K (1993). A novel regulatory element associated with age-dependent expression of the rat androgen receptor gene. J. Biol. Chem. 268(35):26400–8

Suzuki, H., Sato, N., Watabe, Y., Masai, M., Seinu, S., and Shimazaki, J. (1993). Androgen receptor gene mutations in human prostate cancer. J. Steroid Biochem. Mol. Biol. 46:759–65

Symons, R. H. (1992). Small catalytic RNAS. Ann. Rev. Biochem. 61:641–71

Takane, K K, and McPhaul, M. J. (1996). Functional analysis of the human receptor promoter. Mol. Cell. Endocrinol. 119:83–93

Takane, K K, Wilson, J. D., and McPhaul, M. J. (1991). Decreased levels of the androgen receptor in the mature rat phallus are associated with decreased levels of androgen receptor messenger ribonucleic acid. Endocrinology 129(2):1093–100

Takeda, H., Chodak, G., Mutchnik, S., Nakamoto, T., and Chang, C. (1990). Immuno histochemical localization of androgen receptors with mono- and polyclonal antibodies to androgen receptor. J. Endocrinol. 126(1):17–25

Tang, X. B., Hobom, G., and Luo, D. (1994). Ribozyme mediated destruction of influenza A virus in vitro and in vivo. J. Med. Virol. 42(4):385–95

Taplin, M. E., Bubley, G. J., Shuster, T. D., Frantz, M. E., Spooner, A E., Ogata, G. K, Keer, H. N., and Balk, S. P. (1995). Mutation of the androgen-receptor gene in metastatic androgen-independent prostate cancer. N. Engl. J. Med. 332(21):1393–8

Thompson, J. D., Macejak, D., Couture, L., and Seinchcomb, D. T. (1996). Ribozyme in gene therapy. Nature Med. 1:277–8

Tilley, M. D., Marcelli, M., and McPhaul, M. J. (1990). Expression of the human androgen receptor gene utilizes a common promoter in diverse human tissue and cell lines. J. Biol. Chem. 265:13776–81

Tilley, W. D., Marcelli, M., Wilson, J. D., and McPhaul, M. J. (1989). Characterization and expression of a cDNA encoding the human androgen receptor. Proc. Nat'l. Acad. Sci. USA 86(1):327–31

Tohgi, H., Utsugisawa, K, Yamagata, M., and Yoshimura, M. (1995). Effects of age on messenger RNA expression of glucocorticoid, thyroid hormone, androgen, and: estrogen receptors in postmortem human hippocampus. Brain Res. 700(1–2):245–53

Trapman, J., KJaassen, P., Kuiper, G. G., van der Korput, J. A., Faber, P. W., van Rooij, H. C., Geurts van Kassel, A., Voorhorst, M. M., Mulder, E., and Brinkmann, A. O.( 1988). Cloning, structure and expression of a cDNA encoding the human androgen receptor. Biochem. Biophys. Res. Commun. 153(1):241–8

Truss, M., and Beato, M. (1993). Steroid hormone receptors: interaction with deoxyribonucleic acid and transcription factors. Endocr. Rev. 14(4):459–79

Tsai, M. J., and O'Malley, B. W. (1994). Molecular mechanisms of action of steroid/thyroid receptor superfamily members. Ann. Rev. Biochem. 63:451–86

Uhlenbeck, O. C. (1987). A small catalytic oligonucleotide. Nature 328:596–600

Umekita, Y., Hiipakka, R., Kakontis, J., and Liao, S. (1996). Human prostate tumor growth in athymic mice: Inhibition by androgens and stimulation by Finasteride. Proc. Nat'l. Acad. Sci. USA 93:11802–7

Umesono, K, and Evans, R. M. (1989). Determination of target gene specificity for steroid/thyroid hormone receptor. Cell 57:113946 van Laar, J. H., Berrevoets, C. A., Trapman, J., Zegers, N. D., and Brinkmann, A. O. (1991) Hormone-dependent androgen receptor phosphorylation is accompanied by receptor transformation in human lymph node carcinoma of the prostate cells. J. Biol. Chem. 266(6):3734–8

Visakorpi, T., Hyytinen, E., Koivisto, P., Tanner, M, Keinanen, R., Paimberg, C., Palotie, A., Tammela, T., Isola, J., and Kallioniemi, O. P. (1995). In vivo amplification of the androgen receptor gene and progression of human prostate cancer. Nature Genet. 9(4):401–6

Wang, Z. Y., and Deuel, T. F. (1992). An SI sensitive homopurine/homopyrimidine domain in the PDGF-A chain promoter contains a novel binding site for the growth factor-inducible protein EGR-1. Biochem. Biophys. Res. Commun. 188:433–9

Wang, Z. Y., Lin, X H., Nobuyoshi, M., and Veuel, T. F.(1993). Identification of a single-stranded DNA binding protein that interacts with an SI nuclease-sensitive region in the platelet-derived growth factor: a chain gene promoter. J. Biol. Chem. 268:10681–5

Weerasinghe, M., Liem, S. E., Asad, S., Read, S. E., and Joshi, S. (1991). Resistance to human immunodeficiency virus type 1 (HIV-1) infection in human CD4+ lymphocyte-derived cell lines conferred by using retroviral vectors expressing an HIV-1 RNA-specific ribozyme. J. Virol. 65(10):5531–4

Wells, R. O., Collier, D.,k, Hanvey, J. C., Shimizu, M., and Wohlrab, F. (1988). The chemistry and biology of unusual DNA structures adopted by oligopurine, oligopyrimidine sequences. FASEB J. 2:2923–2949

Wilding, G. (1992). The importance of steroid hormones in prostate cancer. Cancer Surv. 14:113–30

Wilson, C. M., and McPhaul, M. J. (1994). A and B forms of the androgen receptor are expressed in a variety of human tissues. Mol. Cell. Endocrinol. 120:51–67

Wilson, C. M., and McPhaul, M. J. (1994). A and B forms of the androgen receptor are present in human genital skin fibroblasts. Proc. Nat'l. Acad. Sci. USA 91 (4):1234–8

Wilson, E. M., and French, F. S. (1995). Androgen receptor defects: historical, clinical, and

What is claimed is:

1. A synthetic ribozyme that cleaves androgen receptor mRNA, wherein said ribozyme comprises the sequence of SEQ ID NO:2.

2. A synthetic ribozyme that cleaves androgen receptor mRNA, wherein said ribozyme is a hammerhead ribozyme that comprises the sequence of SEQ ID NO:2.

3. A synthetic ribozyme that cleaves human androgen receptor mRNA, wherein said ribozyme comprises the sequence of SEQ ID NO:2.

4. The synthetic ribozyme of claim 2, wherein said ribozyme has the sequence of SEQ ID NO:2.

5. The synthetic ribozyme of claim 1 further defined as HR-2 having the sequence as defined in SEQ ID NO: 2.

6. A gene encoding the synthetic ribozyme of claim 1.

7. A vector comprising the gene of claim 6.

8. The vector of claim 7 further defined as comprising a prostate tissue specific promoter.

9. The vector of claim 7, further defined as comprising an RNA polymerase III promoter.

10. The vector of claim 8, wherein said prostate tissue specific promoter is a prostate specific antigen (PSA) promoter.

11. The vector of claim 9, wherein the RNA polymerase III promoter is derived from a small nuclear RNA (U6 RNA) promoter sequence.

12. The vector of claim 7, wherein said gene encodes a synthetic ribozyme having a sequence as defined in SEQ ID NO:2.

13. A method for reducing androgen receptor activity in cultured prostate cells, comprising providing to said cells a preparation comprising the vector of claim 7.

14. A method for inhibiting the proliferation of prostatic cancer cells in vitro, comprising providing to said cells a vector that expresses a synthetic ribozyme in accordance with claim 1.

15. The synthetic ribozyme of claim 3, wherein said ribozyme has the sequence of SEQ ID NO:2.

16. The method of claim 13, wherein said vector expresses a synthetic ribozyme that has the sequence of SEQ ID NO:2.

17. The method of claim 13, wherein said vector comprises an RNA polymerase III promoter.

18. The method of claim 13, wherein said vector comprises a prostate tissue specific promoter.

19. The method of claim 14, wherein said vector expresses a synthetic ribozyme that has the sequence of SEQ ID NO:2.

20. The method of claim 14, wherein said vector comprises an RNA polymerase III promoter.

21. The method of claim 14, wherein said vector comprises a prostate tissue specific promoter.

* * * * *